US009890125B2

(12) United States Patent
Nolan et al.

(10) Patent No.: US 9,890,125 B2
(45) Date of Patent: Feb. 13, 2018

(54) SYNTHESES OF N-HETEROCYCLIC CARBENES AND INTERMEDIATES THEREFOR

(71) Applicant: University Court of the University of St Andrews, St Andrews (GB)

(72) Inventors: Steven P. Nolan, Fife (GB); Sebastien Meiries, Fife (GB)

(73) Assignee: UNIVERSITY COURT OF THE UNIVERSITY OF ST ANDREWS, St. Andrews (GB)

(*) Notice: Subject to any disclaimer, the term of this patent is extended or adjusted under 35 U.S.C. 154(b) by 0 days.

(21) Appl. No.: 14/759,595

(22) PCT Filed: Jan. 6, 2014

(86) PCT No.: PCT/GB2014/050021
§ 371 (c)(1),
(2) Date: Jul. 7, 2015

(87) PCT Pub. No.: WO2014/108671
PCT Pub. Date: Jul. 17, 2014

(65) Prior Publication Data
US 2015/0361049 A1 Dec. 17, 2015
US 2017/0152231 A9 Jun. 1, 2017

(30) Foreign Application Priority Data
Jan. 8, 2013 (GB) .................................. 1300270.4

(51) Int. Cl.
C07C 251/16 (2006.01)
C07C 215/68 (2006.01)
C07C 211/46 (2006.01)
C07C 209/68 (2006.01)
C07C 227/04 (2006.01)
C07D 233/58 (2006.01)

(52) U.S. Cl.
CPC .......... C07D 233/58 (2013.01); C07C 211/46 (2013.01); C07C 215/68 (2013.01); C07C 251/16 (2013.01)

(58) Field of Classification Search
CPC ... C07C 251/16; C07C 215/68; C07C 211/46; C07C 209/68; C07C 227/04
USPC ......................................................... 564/305
See application file for complete search history.

(56) References Cited

U.S. PATENT DOCUMENTS

| 4,503,211 A | 3/1985 | Robins |
| 7,109,348 B1 | 9/2006 | Nolan |
| 2010/0137308 A1* | 6/2010 | Gaillard ............... C07D 241/44 514/234.8 |

FOREIGN PATENT DOCUMENTS

| CN | 102702165 A | 10/2012 |
| DE | 2730620 A1 | 1/1979 |
| WO | 2007046611 A1 | 4/2007 |

OTHER PUBLICATIONS

Dible, Benjamin R., et al.; "Remote Substitution on N-Heterocyclic Carbenes Heightens the Catalytic Reactivity of Their Palladium Complexes," Organometallics, 2011, pp. 5123-5132, vol. 30.
Organ, Michael G., et al.; "Pd-PEPPSI-IPent: An Active, Sterically Demanding Cross-Coupling Catalyst and Its Application in the Synthesis of Tetra-Ortho-Substituted Biaryls," Angewandte Chemie, 2009, pp. 2419-2423, vol. 121.
Steele, Barry R., et al.; "Synthesis of New Sterically Hindered Anilines," European Journal of Organic Chemistry, 2007, pp. 3091-3094.
Meiries, Sebastien, et al.; "Large yet Flexible N-Heterocyclic Carbene Ligands for Palladium Catalysis," Chemistry A European Journal, 2013, pp. 17358-17368, vol. 19.
Le Duc, Gaetan, et al.; "Effect of Electronic Enrichment of NHCs on the Catalytic Activity of [Pd(NHC)(acac)Cl] in Buchwald-Hartwig Coupling," Organometallics, 2013, pp. 7547-7551, vol. 32.
Huang, Jinkun, et al.; Efficient Cross-Coupling of Aryl Chlorides with Aryl Grignard Reagents (Kumada Reaction) Mediated by a Palladium/Imidazolium Chloride System, Journal of the American Chemical Society, 1999, pp. 9889-9890, vol. 121.
U.K. Intellectual Property Office; Search Report for U.K. Application No. GB1300270.4 dated May 15, 2013, 2 Pages.
JIPO; Office Action for Japanese Application No. 2015-551220, dated Sep. 12, 2017, 4 pages.
Acta Polymerica Sinica, Feb. 2003, vol. No. 1, pp. 45-51.
Tetrahedron, 1999, vol. 55, pp. 14523-14534.

* cited by examiner

*Primary Examiner* — Matthew Coughlin
*Assistant Examiner* — Sagar Patel
(74) *Attorney, Agent, or Firm* — Christopher J. Knors; Moore & Van Allen, PLLC

(57) ABSTRACT

A method of preparing a 2,6 disubstituted anilines includes, reacting a 2-amino isophthalic acid diester with sufficient Grignard reagent $R_2CH_2MgX$ to form the corresponding diol product, dehydrating the diol product to the corresponding dialkene; and hydrogenating the diol product to form the corresponding aniline. The 2,6 disubstituted anilines can be used to produce N-Heterocyclic Carbenes (NHCs). The NHCs can find application in various fields such as organic synthesis, catalysis and macromolecular chemistry. Palladium catalysts containing the NHCs are also described.

14 Claims, No Drawings

SYNTHESES OF N-HETEROCYCLIC CARBENES AND INTERMEDIATES THEREFOR

CROSS-REFERENCE TO RELATED APPLICATIONS

This application is filed under the provisions of 35 U.S.C. § 371 and claims the benefit of International Patent Application No. PCT/GB2014/050021, filed on Jan. 6, 2014, which claims the benefit of Patent Application No. 1300270.4, filed in Great Britain on Jan. 8, 2013; all of which are hereby incorporated by reference in their entirety.

FIELD OF THE INVENTION

The present invention relates to the synthesis of N-heterocyclic carbenes, including the synthesis of 1,3 substituted anilines as intermediates that are prepared via novel diol intermediates.

BACKGROUND TO THE INVENTION

N-Heterocyclic carbenes (NHCs) are considered as an important class of compounds which have found application in various fields such as organic synthesis, catalysis and macromolecular chemistry. In the field of catalysis, NHC ligands are often compared with phosphine-based ligands which still remain more commonly used. However, unlike their phosphine analogues, metal-NHC complexes are now recognized for their unique properties and their higher air and moisture stability, particularly in the case of palladium and ruthenium-NHC catalysis.

The importance of NHC ligands in catalysis is related to their σ-donating properties as well as their steric hindrance which has strong effects on both oxidative additions and reductive eliminations in metal-catalyzed organometallic cross-couplings. Spectacular reactivity has been attributed to a "flexible steric bulk" in which the ligands can adjust towards incoming substrates, while enabling the stabilization of low-valent active intermediates.

As an example, the bulky IPr NHC ligand (A, below) reported by Nolan (Ref 1) exhibits excellent properties in catalysis. However the rigidity of the IPr ligand can be envisaged as a significant limitation and the design of new NHC ligands possessing flexible bulk appears as a major challenge.

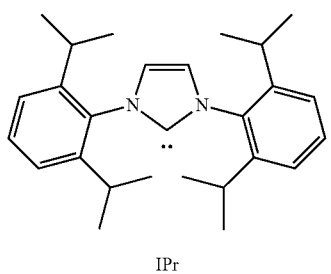

IPr

A

DESCRIPTION OF THE INVENTION

According to a first aspect the present invention provides a method of preparing N-heterocyclic carbenes (NHCs), the method comprising reacting an aniline of general formula I:

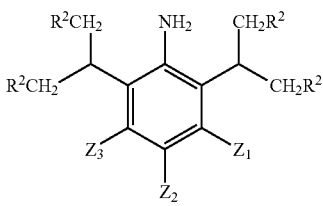

I wherein each group $R^2$ is the same; and is selected from H, methyl, ethyl, n-propyl and

wherein either;
$R^3$ is H and $R^4$ is an alkyl, for example C2 to C10 alkyl or even C2 to C5 alkyl; or
each of $R^3$, $R^4$ are an independently selected alkyl, for example C1 to C10 alkyl or even C1 to C5 alkyl; and
each group $Z_1$, $Z_2$ and $Z_3$ is independently selected from —H, —I, —CF$_3$, —OR$^5$, —R$^6$ and —NR$^7_2$;
wherein each group $R^5$, $R^6$ or $R^7$ is independently selected from the group consisting of: alkyl that may be unsaturated, substituted alkyl that may be unsaturated, aryl, substituted aryl, aralkyl and substituted aralkyl, for example C1 to C10 alkyl or even C2 to C5 alkyl;
with glyoxal to form a diimine of general formula II;

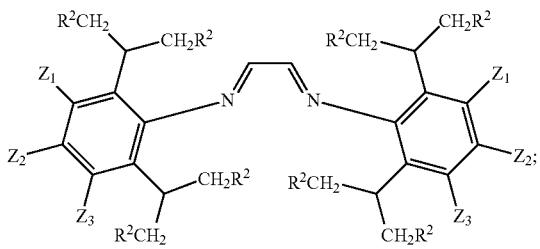

II cyclising the diimine of structure II, to form an imidazolium salt of structure III;

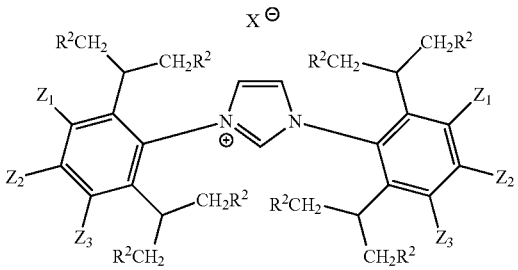

III wherein X⁻ is an anion for example halogen, such as chloride, bromide or iodide; and reacting the imidazolium salt of structure III with a base to form the NHC.

Where groups $R^3$ or $R^4$ are alkyl they are typically straight-chain alkyl and unsubstituted, but they may be any one or more of branched, cyclic, unsaturated and substituted, as discussed hereafter. Preferably $R^3$ is H and $R^4$ is straight chain saturated unsubstituted alkyl.

The groups $Z_1$, $Z_2$ and $Z_3$ may preferably be H. However the properties of the NHC may be adjusted by introducing different groups Z into the anilines I.

Where adjustment of the properties of the NHC by substituent Z is desired then, for example, the groups $Z_1$, and $Z_3$ may preferably and conveniently be H and the $Z_2$ substituent (i.e. the substituent para to the aniline —$NH_2$ function) may be different e.g. one of —I, —$CF_3$, —$OR^5$ and —$R^6$.

Methyl and methoxy (-Me and —OMe) substituents are typical examples of —$R^6$ and —$OR^5$ for the groups Z. Other groups Z may include —$NMe_2$ or —$NR^7{}_2$; wherein $R^7$ may be alkyl aryl, or aralkyl, for example C1 to C10 alkyl or even C1 to C5 alkyl.

The reaction of anilines of structure I with glyoxal may be carried out using a glyoxal in water solution, for example a 40% glyoxal in water solution.

The cyclisation of the diimine II to imadazolium salt of structure III may be carried out by using paraformaldehyde as the source of carbon to complete the imidazolinium ring structure. For example by reaction of the diimine II with paraformaldehyde in a suitable solvent system using a protic acid or another source of $X^-$ such as anhydrous HCl, or trimethylsilyl chloride (TMSCl) which provides the source of group $X^-$ (chloride in these examples). Zinc chloride may be used to assist the reaction with either HCl or TMSCl.

Ether type solvents such as THF and/or dioxane may be employed. For example the procedure may be adding a solution of anhydrous HCl in dioxane to the diimine II and paraformaldehyde in THF. Other solvents may be used, for example ethyl acetate (EtOAc) can be used effectively when TMSCl is the chloride source. Elevated temperatures for example from 50° C. to 100° C. may be employed e.g. about 70° C. (say ±5° C.) for a THF/dioxane solvent system is convenient.

The imidazolinium salts of structure III may then be converted to N-heterocyclic carbenes of structure IV:

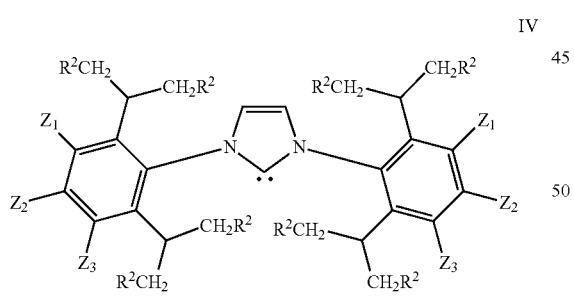

IV by use of base to remove HX in the known manner. Typically sodium hydride (NaH) in a suitable solvent such as tetrahydrofuran (THF) may be employed, together with a catalytic amount of potassium t-butoxide (KO'Bu).

The NHCs of formula IV may be described as ITent N-heterocyclic carbenes (Tent stands for "tentacular" where the groups ortho to the nitrogen on the benzene rings form tentacle like bulky groups). Previously described examples are IPr:—(N,N'-bis(2,6-diisopropylphenyl)imidazol-2-ylidene) and IPent:—(N,N'-bis[2,6-(dipentan-3-yl)phenyl] imidazol-2-ylidene) NHCs. The abbreviation after the I in the ITent nomenclature refers to the alkyl groups on the benzene rings (Pr denoting isopropyl, Pent denoting pent-3-yl, Hept denoting hept-4-yl, and Non denoting non-5-yl etc). A convenient nomenclature for the corresponding imidazolium salts of formula III, where X is chloride, is for example IPr.HCl for the precursor to IPr.

Typically the NHC will be generated in the presence of a metal containing precursor to a desired NHC containing compound. Typically the NHC containing compound is a metal complex, usually for use as a catalyst or a catalyst precursor.

Typical preparations can include the exchange of a ligand on a metal compound with the NHC. In such cases the ligand can act as the base that generates the NHC.

For example $Pd(acac)_2$ where acac is the acetonylacetonato ligand, can be reacted with an imidazolium salt of structure III to provide NHCs of structure IV above to form complexes of the form Pd(acac)(ITent)Cl. The reaction may be carried out in a suitable solvent, such as an ether, for example 1,4-dioxane. Typically the reaction is carried out at elevated temperature, for example at the boiling temperature of the solvent.

The reaction can be expressed as;

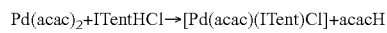

Pd(acac)$_2$+ITentHCl→[Pd(acac)(ITent)Cl]+acacH

Exemplary complexes include those where ITent is one of, for example, IPent, IHept, INon i.e. the N-heterocyclic carbenes IV corresponding to the imidazolium salts IIIa, IIIb and IIIc of scheme 2, below. For further example the complexes may include methoxy substituents in the para position i.e. $Z_2$ is —OMe and $Z_1$ and $Z_3$ are H in NHC ligands of structure IV in these complexes. Such complexes may conveniently be expressed as Pd(acac)(ITent-OMe)Cl where —OMe refers to both $Z_2$ groups being methoxy substituents.

Exemplary complexes that can find use as catalysts include complexes shown below:

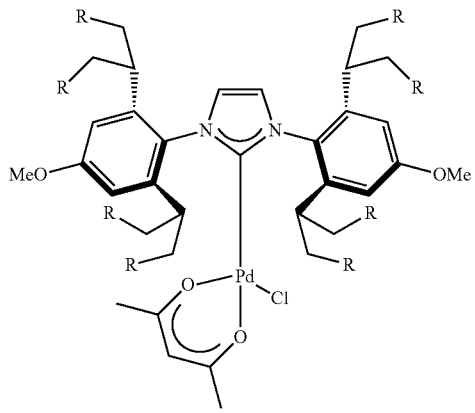

[Pd(ITent-OMe)(acac)Cl]
IPent-OMe; R = Me
IHept-OMe; R = Et
INon-OMe; R = n-Pr

These complexes with methoxy substituted NHCs can find use in Buchwald-Hartwig arylamination reactions even with substrates generally considered disfavoured for the transformation. For example coupling of electron rich aryl halides with electron deficient anilines such as methoxy substituted aryl halides and fluoro substituted anilines. Exemplary results are described in detail hereafter.

For further example gold complexes of the form Au (ITent)Cl where ITent is for example one of IPent, IHept, INon may be prepared from similar exchange reactions such as:

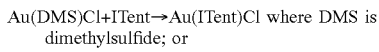 Au(DMS)Cl+ITent→Au(ITent)Cl where DMS is dimethylsulfide; or

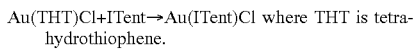 Au(THT)Cl+ITent→Au(ITent)Cl where THT is tetra-hydrothiophene.

Thus the inventive methods described herein include the preparation of an NHC and metal containing complex. Typically the metal and NHC containing complex can find use as a catalyst or catalyst precursor.

The method comprises generating an NHC by the methods described herein and complexing the NHC to a metal to provide a metal and NHC containing complex. Typically the NHC coordinates to the metal.

Typical metals include Pd, Pt, Ru, Cu, Ag, Rh Ir and Au. Generally the complex will have ligands other than an NHC as for existing NHC containing complexes.

More generally the method produces complexes of the form M(NHC)L$_n$ where M is a metal; NHC is an N-heterocyclic carbene as described herein; L is a ligand; and n is the number of ligands L. The number (n) of ligands L depends on the nature of each L, the metal M and its oxidation state; as will be understood by the skilled person. Each L may be the same or different and coordinating or non-coordinating. Typically n will be from 1 to 6. Exemplary ligands L can include halogen, and those containing at least one of P, N, O and S, where the atom P, N, O or S coordinates to the metal. Non-coordinating ligands are typically anions such as halide. Other ligands may include an unsaturated carbon-carbon bond such as C=C or C≡C that coordinates to the metal (e.g. cinnamyl).

Only a few anilines of structure I have been reported previously. The precursor to IPr, the aniline of structure V below where the groups R$^2$ and the Z groups are all H, is commercially available.

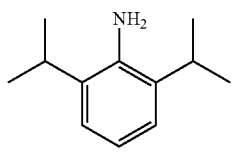

V

The conversion of aniline V to Pr, via the corresponding imidazolinium salt. is described in U.S. Pat. No. 7,109,348 (Nolan).

The aniline of structure VI below, where the groups R$^2$ are methyl and the Z groups are all H, is also known.

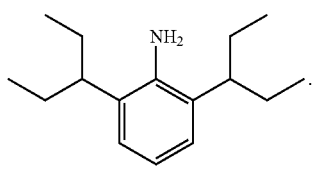

VI

Prior art methods of manufacture of aniline VI has been described by Steele (Ref 2) and involves the use of a relatively complex "superbase" system—n-BuLi/LiK (OCH$_2$CH$_2$NMe$_2$)/Mg(OCH$_2$CH$_2$OEt)$_2$ to add ethylene gas to 1,3 dimethylaniline. The purification of the product also requires fractional distillation.

Although the tentacular NHC "IPent"—formula IX;

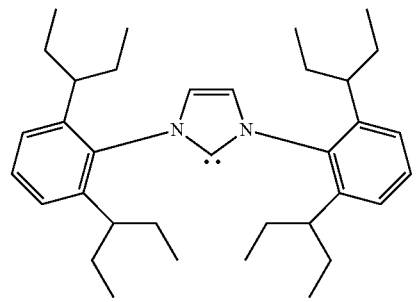

IX where groups R$^2$ in formula IV are methyl and the Z groups are all H, has been previously reported, no information regarding the synthetic route was provided. (Ref 3).

Anilines of Structures

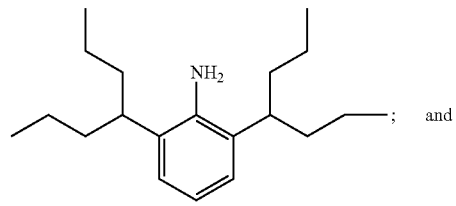

VII

; and

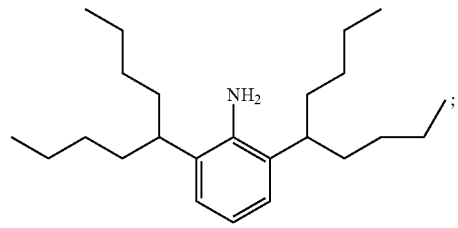

VIII

;

wherein the groups R$^2$ in formula I are ethyl and n-propyl respectively constitute further aspects of the invention, as do their corresponding diimines II, imidazolium salts III and N-heterocyclic carbenes IV.

The present invention provides convenient and general methods for the manufacture of anilines of formula I, thus allowing the convenient preparation of NHC's of formula IV. The NHCs can be used, for example to prepare metal NHC complexes for use in e.g. catalysis.

The present invention provides a method of preparing a 2,6 disubstituted aniline, the method comprising:

reacting a 2-amino isophthalic acid diester with sufficient Grignard reagent R$^2$CH$_2$MgX to form the corresponding diol product from reaction at the diester functions; wherein R$^2$ is selected from H, methyl, ethyl, n-propyl and

wherein either;

R$^3$ is H and R$^4$ is an alkyl, for example C2 to C10 alkyl or even C2 to C5 alkyl; or each of $R^3$, $R^4$ are an independently selected alkyl, for example C1 to C10 alkyl or even C1 to C5 alkyl; and X is halogen (chloride, bromide or iodide);

dehydrating the diol product to the corresponding dialkene; and hydrogenating the dialkene product to form the corresponding aniline.

Conveniently the 2-amino isophthalic acid diester employed has H in the meta and para (with respect to amino) positions of the benzene ring.

Thus the present invention provides a method of preparing an aniline of general formula I:

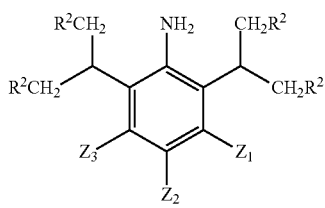

I wherein each group $R^2$ is the same and is selected from H, methyl, ethyl, n-propyl and

wherein either;
 $R^3$ is H and $R^4$ is an alkyl, for example C2 to C10 alkyl or even C2 to C5 alkyl; or
 each of $R^3$, $R^4$ are an independently selected alkyl, for example C1 to C10 alkyl or even C1 to C5 alkyl; and
 each group $Z_1$, $Z_2$ and $Z_3$ is independently selected from the group consisting of —H, —I, —$CF_3$, —$OR^5$, —$R^6$ and —$NR^7_2$, wherein each group $R^5$, $R^6$ or $R^7$ is independently selected from the group consisting of: alkyl that may be unsaturated, substituted alkyl that may be unsaturated, aryl, substituted aryl, aralkyl and substituted aralkyl.

Each group $R^5$, $R^6$ or $R^7$ may be for example C1 to C10 alkyl or even C1 to C5 alkyl.

If substitution is required to provide one or more groups Z in general formula I that is not H, then substitution of one or more H by group Z may be achieved after an aniline with H in all three meta and para positions has been made.

For example via electrophilic aromatic substitution carried out in the known manner (and followed if necessary by modification or replacement of the substituent(s) first added) to produce the group Z. For example, a para Z substituent ($Z_2$) may be introduced via halogenation, nitration or Friedel-Crafts alkylation or acylation procedures on the aniline followed by subsequent modifications as required, providing the desired group $Z_2$.

Alternatively a 2-amino isophthalic acid diester already substituted with one or more groups Z may be employed in the method.

With either alternative an initially introduced group Z may be modified at any convenient stage in the synthetic route to the NHC. For example on the intermediates diimines of formula II or imidazolium salts of formula III discussed above.

As an example, anilines of general formula I where all three Z substituents are H may be readily converted to the corresponding anilines where the para group $Z_2$ is iodine by halogenation in the known manner for iodides; for example, by reaction with iodine in the presence of a base (e.g. aqueous sodium carbonate and iodine reacting with the aniline, which may be in a solvent such as cyclohexane). The reaction may be carried out at ambient or elevated temperature.

Subsequent conversion of the iodo function to methoxy (—OMe); or other alkoxy substituents; can be conveniently carried out after the iodo containing aniline has been converted to the corresponding diimine of formula II as discussed hereafter and with reference to particular embodiments. For example by reaction with methanol (or other alcohol) in the presence of base and a copper salt (e.g., a caesium carbonate, phenanthroline and copper iodide system at elevated temperature in a sealed vessel such as a sealed tube). For example with methanol as solvent at between 80 and 160° C. or even at between 100 and 140° C. or at about 120° C.

If desired poly-iodo anilines (where more than one of substituents Z is iodine) may be converted to the corresponding diimines of formula II and then the same approach used to convert the iodo functions to methoxy or other alkoxy.

The p-methoxy diimines of formula II may be readily converted to the p-methoxy anilines of formula I by reaction with acid; for example hydrochloric acid. Reaction may be carried out for example in aqueous hydrochloric acid (e.g. 37%) in the presence of a suitable solvent such as THF at ambient or elevated temperature (e.g. at about 100 C). Thus the diimine function can act as a protecting group in a procedure to prepare substituted anilines of formula I with, for example, methoxy or other alkoxy substituents at one or more of the positions Z.

The ester functions of the 2-amino isophthalic acid diester may have any substituent attached to the ether linkage of the carboxylate function to form the two ester functions.

Formula X below shows substituents forming the ester functions (shown as $R^1$) on a 2-amino isophthalic acid diester where all groups Z are H:

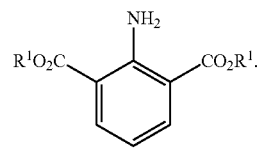

X

Typically and conveniently groups $R^1$ will be the same, but they could be different. $R^1$ may be an alkyl group. Other alternatives include benzyl or substituted benzyl. Alkyl groups $R^1$ may be conveniently C1 to C15 alkyl, C1 to 010 alkyl or even C1 to C5 alkyl. Alkyl groups $R^1$ may be linear or branched and may be substituted.

Thus the present invention provides a method of preparing anilines of general formula I, the method comprising:
 reacting an aniline of formula X;

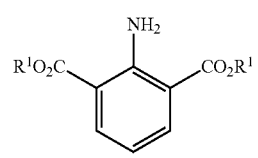

X wherein each group R¹ is independently selected from the group alkyl, for example C1 to C15 alkyl, C1 to C10 alkyl, C1 to C5 alkyl, and benzyl or substituted benzyl with a Grignard reagent of the form R²CH₂MgX, wherein each group R² has the same meaning as before and X is a halogen selected from I, Cl and Br, to form a diol of formula XI;

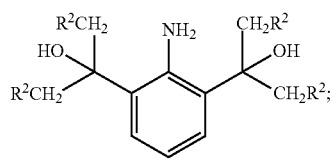

XI dehydrating the diol of formula XI to form a dialkene; and hydrogenation of the dialkene to form an aniline of general formula I.

Where one or more of the groups Z in an aniline of general formula I is not to be H, the method further comprises carrying out one or more substitution reactions on the initial aniline formed to provide the required group or groups Z.

Alternatively the method may be carried out with one or more groups Z (where at least one Z is not H) already in place, i.e. carrying out the procedure starting with a diester of general formula Xa:

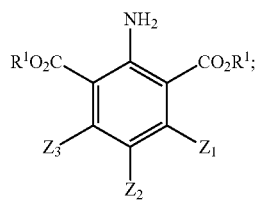

Xa wherein the groups R¹, $Z_1$, $Z_2$ and $Z_3$ have the same meaning as before and at least one of the groups Z is not H.

The dehydration of the diols in the method, for example of the diols of general formula XI, to form a corresponding dialkene may be carried out by the use of any suitable dehydrating agent, for example by use of concentrated sulphuric acid, typically in a suitable solvent such as THF or toluene. Typically a variable mixture of E and Z isomers is formed, which can readily be hydrogenated to the desired aniline.

Hydrogenation of the dialkene products may be carried out by use of H₂, for example H₂ in the presence of a suitable catalyst, such as palladium on carbon (Pd/C).

The diol intermediates such as XI or more generally of formula XIa:

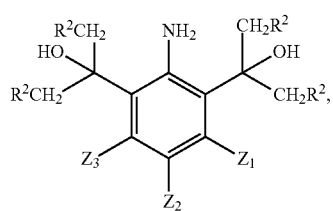

XIa where the substituents R² and $Z_1$, $Z_2$, and $Z_3$ have the same meaning as before; allow convenient preparation of the anilines I and hence of N-heterocyclic carbenes IV via the diimines II and imidazolium salts III constitute a further aspect of the present invention.

The present invention also provides a convenient synthesis of diester anilines of formula X or of formula Xa (esters of 2-aminoisophthalic acid), the method starting from the commercially available 2-nitro-m-xylene XII. For example the method comprises:

the bis-oxidation of 2-nitro-m-xylene XII to 2-nitroisophthalic acid XIII;

the conversion of 2-nitroisophthalic acid XIII to its corresponding diester XIV (typically the dimethyl ester where R¹ is methyl); and the reduction of the nitro diester XIV to the diester aniline X. Where a diester of formula Xa is desired a substituted 2-nitro-m-xylene may be employed or one of the other intermediates in the synthetic route may be substitute.

Attempts to introduce groups R² via a Grignard reaction on the nitro-substituted diesters XIV were unsuccessful. It is therefore convenient to reduce the nitro function to amine before esterification, to provide compounds of formula X.

The method is illustrated in Scheme 1, below, showing the convenient procedure to the diester anilines X and continuing through to the preparation of anilines of formula I. In these examples each group Z is H.

A one-pot version of the dehydration-hydrogenation sequence of steps v and vi may be carried out but lower product purity may be obtained. The illustrated 6-step synthetic route allows for the preparation of multigram quantities of anilines I with minimal purification procedures being required.

The bis-oxidation of 2-nitro-m-xylene XII to 2-nitroisophthalic acid XIII may be carried out by an Etard type reaction, conveniently employing alkaline potassium permanganate as the oxidising reagent in this case (e.g. with sodium hydroxide employed as the base).

The esterification to form diesters XIV can be carried out with a selected alcohol R¹OH in the usual way, for example to form the dimethyl diester by using methanol and acid catalyst such as sulphuric acid. Other esterification procedures, known to the skilled person, may be employed.

The reduction of nitro diesters XIV to diester anilines X may be carried out by hydrogen in the presence of a suitable catalyst such as palladium on carbon.

Scheme 1

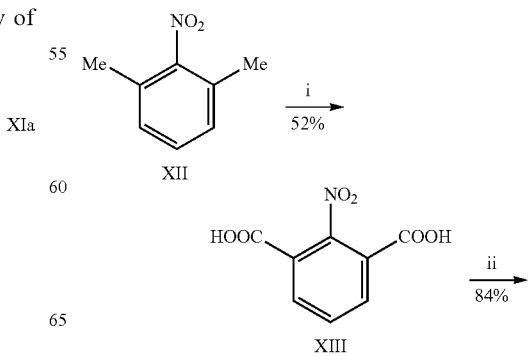

-continued

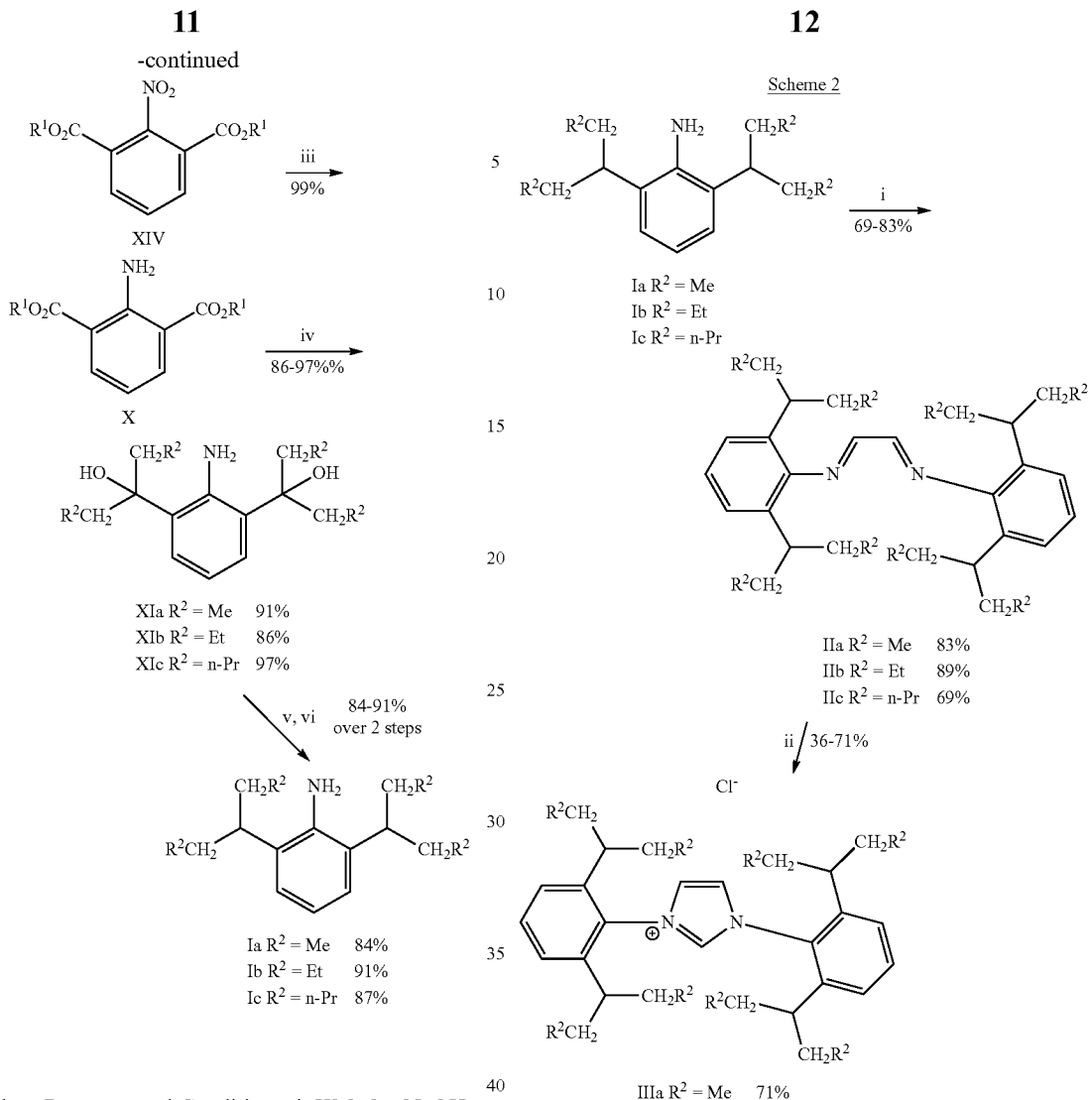

Scheme 2

IIa R² = Me  83%
IIb R² = Et  89%
IIc R² = n-Pr  69%

IIIa R² = Me  71%
IIIb R² = Et  47%
IIIc R² = n-Pr  36%

XIa R² = Me  91%
XIb R² = Et  86%
XIc R² = n-Pr  97%

Ia R² = Me  84%
Ib R² = Et  91%
Ic R² = n-Pr  87%

Ia R² = Me
Ib R² = Et
Ic R² = n-Pr

[Exemplary Reagents and Conditions. i, $KMnO_4$, NaOH, $H_2O$, reflux, 12 h; ii, $H_2SO_4$, MeOH, reflux, overnight; iii, 10% Pd/C, $H_2$, AcOEt, rt, 20 h; iv, alkylbromide RBr (R=Et, n-Pr, n-Bu), Mg, THF, 0° C. to rt, 1-2 h; v, $H_2SO_4$, THF, 100° C., 1-2 h; vi, 10% Pd/C, $H_2$, EtOH, reflux, 6 to 48 h.]

It will be appreciated that one or more of the meta and para substituent hydrogens on the benzene ring in the structures of Scheme 1 may be substituted by one of the alternative groups Z described herein, at a convenient point in the synthetic route.

The exemplary reagents and reaction conditions provided above with Scheme 1 are discussed in more detail under the heading "Description of Some Preferred Embodiments and Experimental Results", below.

Having prepared the anilines I by the convenient route exemplified in Scheme 1, they can then be used to prepare the imidazolium salts Ill as illustrated below in Scheme 2, where $X^-$ is chloride in these examples. If desired substituents Z (where one or more group Z is not H) as discussed above, especially $Z_2$ (para) substituents, may be introduced first. The imidazolium salts III can then be used to prepare NHCs by the action of base as discussed above. Thus the route exemplified in schemes 1 and 2 provides an effective synthesis of NHCs of formula IV (and their precursors) from the commercially available 2-nitro-m-xylene XII.

[Exemplary Reagents and Conditions. i, glyoxal (40% in $H_2O$), HCOOH, MeOH, rt, 3-5 h; ii, $(CHO)_n$, $ZnCl_2$, HCl (4M in dioxane), 70° C., 3 h.]

As an alternative to the use of anilines of general formula I

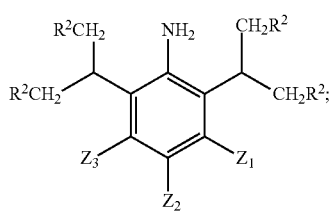

I to prepare useful NHCs in accordance with the invention, the intermediate dialkene products prepared by the dehydration of the dial intermediates of formula XI may be employed. These dehydrated products are of general formula XV:

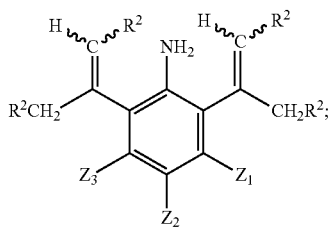

XV where the groups $R^2$ and Z ($Z_1$, $Z_2$, $Z_3$) have the same meanings as before. The stereochemistry about both the double bonds can vary as suggested by the wavy bond lines to H and $R^2$. As discussed above typically mixtures of Z and E isomers are formed on dehydration of the diols XI (except where $R^2$ is H). If desired these isomers may be isolated e.g. by chromatography or recrystallisation techniques. Alternatively a mixture may be used. It will be understood that unless the context dictates otherwise structure XV means one or more of the isomers possible by varying the stereochemistry about the double bonds.

Typically the procedure produces a preponderance of the isomer where both double bonds have the E conformation as in formula XV(E2) below.

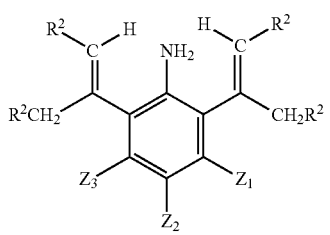

XV(E2)

The compounds of general formula XV (or XV(E2)) may be converted to diimines and imidazolium salts and hence to NHCs and catalysts containing the corresponding NHCs by the same procedures as described for anilines of general formula I (Scheme 2) This is illustrated in Scheme 3 for a compound XVa where the groups Z are H. The same route may be employed for compounds of general formula XV(E2).

Scheme 3

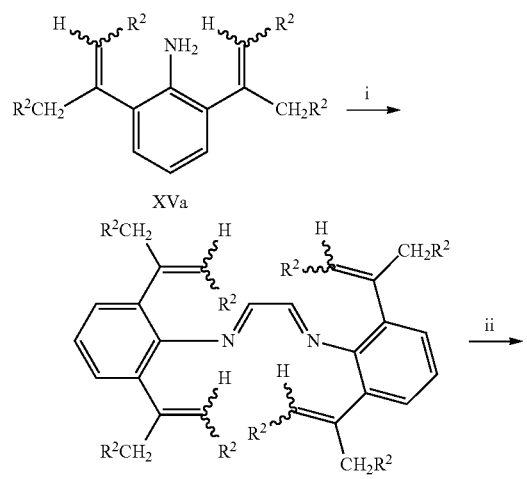

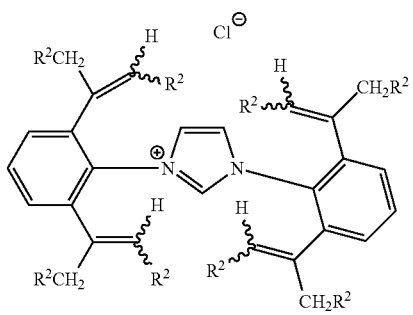

Thus the present invention provides a method of manufacture of anilines of general formula XV, the method comprising reacting a 2-amino isophthalic acid diester with sufficient Grignard reagent $R^2CH_2MgX$, wherein $R^2$ has the same meaning as before and X is halogen (chloride, bromide or iodide), to form the corresponding diol product from reaction at the diester functions; and dehydrating the diol product to the corresponding dialkene of formula XV.

Where groups Z other than H are desired then they may be introduced after forming an aniline of general formula XVa (Scheme 3). This can be done in the same manner as described above when forming anilines of formula I with one or more Z groups that are not H. Alternatively the 2-amino isophthalic acid diester may have the desired Z group or groups already present. As discussed above with respect to the anilines of formula I groups Z may be modified at any convenient point in the synthetic route to the corresponding NHCs.

Thus the present invention provides a method of preparing N-heterocyclic carbenes (NHCs), the method comprising:

reacting an aniline of general formula XV as described above with glyoxal to form a diimine of general formula XVI;

XVI

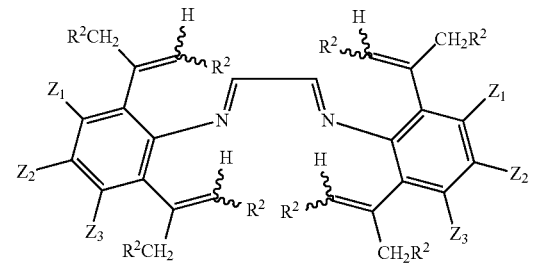

cyclising the diimine of structure XVI, to form an imidazolium salt of structure XVII;

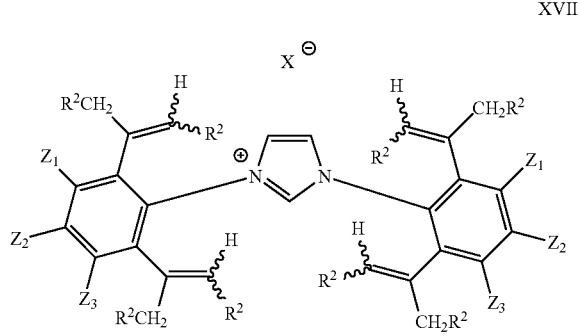

XVII

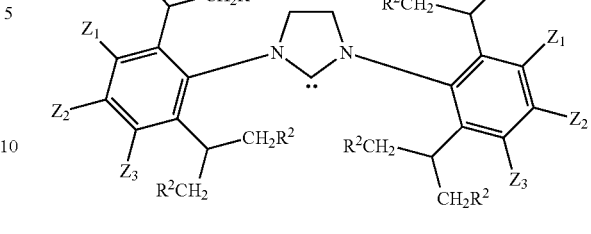

IVs wherein X⁻ is an anion for example halogen, such as chloride, bromide or iodide; and reacting the imidazolium salt of structure XVI with a base to form the corresponding NHC.

Typically the NHC will be generated in the presence of a metal containing precursor to a desired NHC containing compound, usually intended for use as a catalyst or a catalyst precursor.

Typical preparations can include the exchange of a ligand on a metal compound with the NHC. The same procedures described above for the preparation of NHCs of structure IV may be used to prepare NHCs of structure XVIII or XVIII (E2) below; and the corresponding metal containing complexes M(NHC)L$_n$:

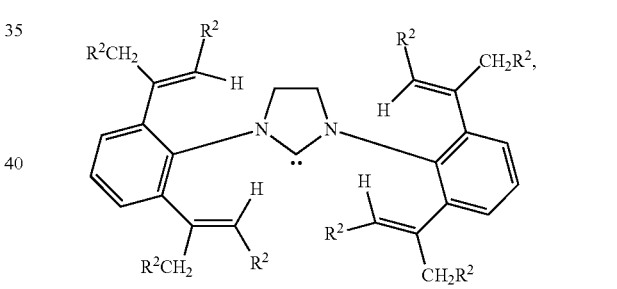

XVIIIs

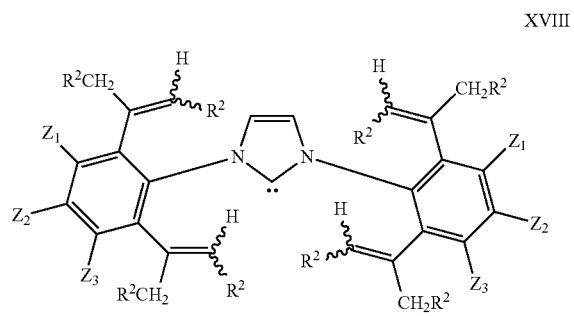

XVIII

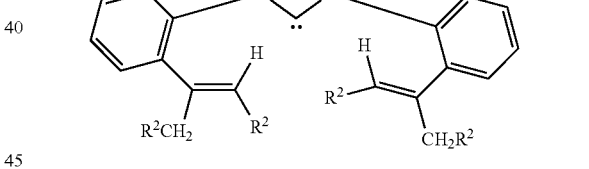

XVIII(E2)s where the substituents $R^2$ and $Z$ have the same meanings as before. These NHCs may be used to make corresponding metal containing complexes M(NHC)L$_n$.

To provide these structures the methods described above may include the reduction of the corresponding intermediate diazabutadiene compound; for example of formula II:

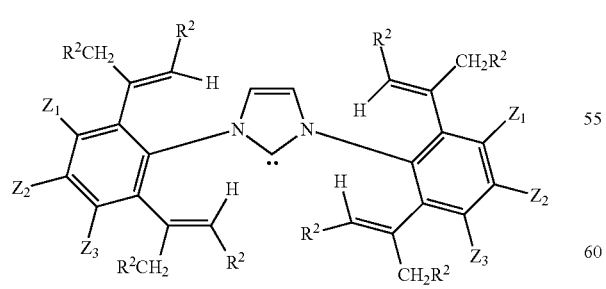

XVIII(E2)

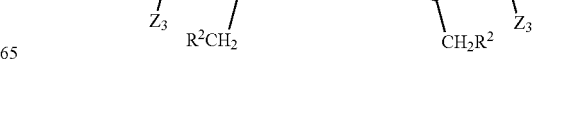

II

As a yet further alternative the methods described herein may be used to form N-heterocyclic carbenes wherein the ring containing the two nitrogen atoms is saturated i.e. a structure according to one of the following:

to the corresponding diamine; for example of formula XIX:

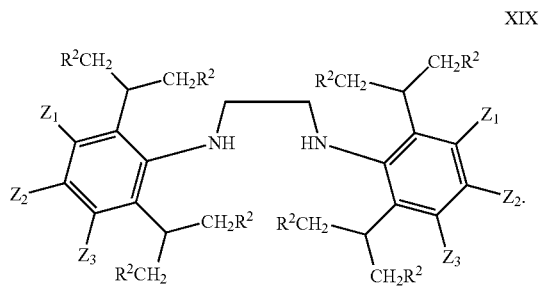

XIX

This may be accomplished by reduction using a suitable reducing agent such as dibal (diisobutylaluminium hydride) in a suitable solvent, such as THF or toluene. The reduction may also be carried out using lithium aluminium hydride in a suitable solvent such as ethers (e.g. dioxane, THF, or mixtures thereof). The diamine can then be cyclised to the corresponding dihydroimidazolinium salt using a suitable one carbon source (e.g. triethylorthoformate) in the present of an acid HX. For example hydrochloric acid, which may be supplied in a solvent such as an ether, for example dioxane.

An exemplary synthesis is shown below for the production of the SIPr-OMe dihydroimidazolinium salt (SIPr-OMe.HCl) The nomenclature "S" indicating that the imidazolinium ring has been saturated by the reduction step and the term —OMe indicating a methoxy substituent at the para ($Z_2$) position of both phenyl rings.

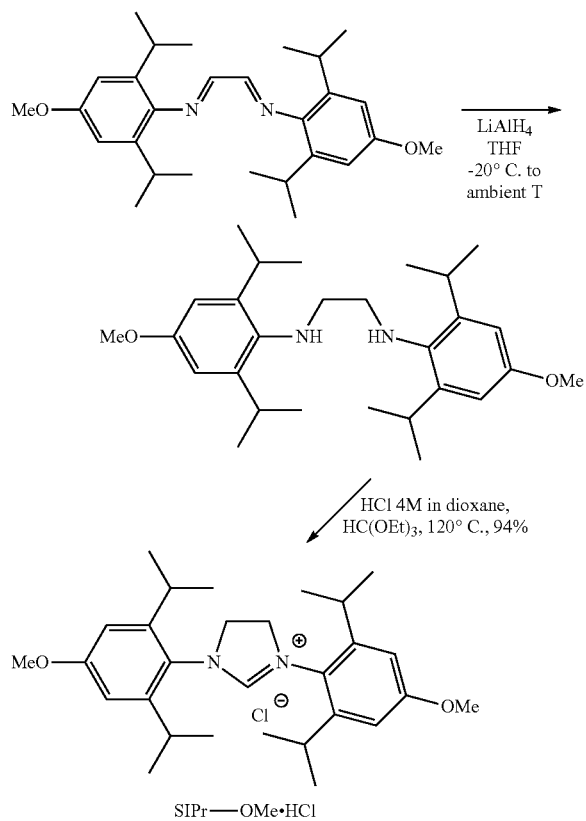

The resulting dihydroimidazolinium salts, for example of formula XX or XXa;

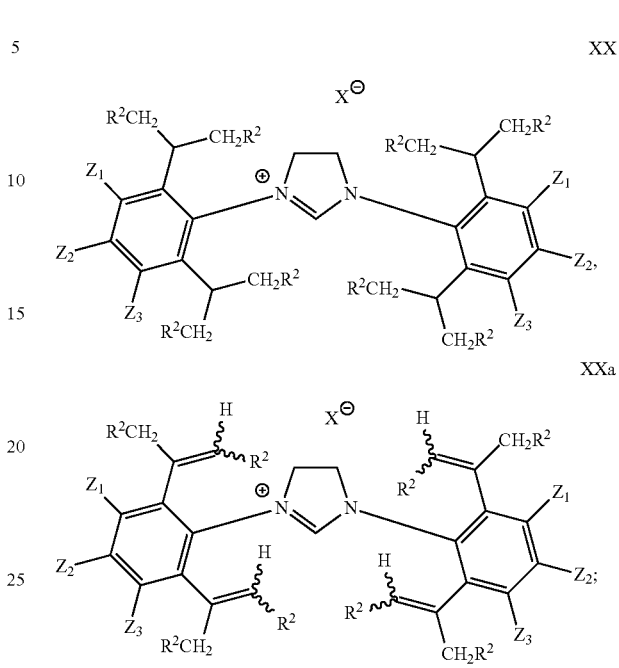

can then be converted to the corresponding NHC as described above for the imidazolium salts, such as those of formula III or formula XVII. The introduction and (if desired) subsequent modification of groups Z (where Z is not H) may be carried out at convenient points in the described synthetic route.

Throughout the description of the present invention groups R ($R^1$, $R^2$ etc) are defined as alkyl, aryl or benzyl. Except where otherwise specified, or the context dictates to the contrary, by alkyl is meant herein a hydrocarbyl radical, which may be straight-chain, cyclic, branched or unsaturated (typically straight-chain and saturated). Typically alkyl groups comprise from 1 to 25 carbon atoms, more usually 1 to 10 carbon atoms, more usually still 1 to 6 carbon atoms, it being of course understood that the lower limit to the number of carbon atoms in cycloalkyl and cycloalkylene groups is 3.

Where an alkyl group is unsaturated (i.e. is an alkenyl or alkynyl group) it may have one or more sites of unsaturation, constituted by carbon-carbon double bonds or carbon-carbon triple bonds. The presence of a carbon-carbon double bond provides an alkenyl group; the presence of a carbon-carbon triple bond provides an alkynyl group. Typically, alkenyl and alkynyl groups comprise from 2 to 25 carbon atoms, more usually 2 to 10 carbon atoms, more usually still 2 to 5 carbon atoms. Examples of alkenyl groups include vinyl, styryl and acrylate; an example of an alkynyl group is propargyl. For the avoidance of any doubt, a hydrocarbyl radical comprising both a carbon-carbon double bond and a carbon-carbon triple bond may be regarded as both an alkenyl and an alkynyl group.

Except where otherwise specified or the context dictates otherwise, groups R may be substituted, for example once, twice, or three times, e.g. once, i.e. formally replacing one or more hydrogen atoms of the group. Examples of such substituents are hydroxy, amino, halo, aryl, (including heteroaryl), nitro, alkoxy, alkylthio, cyano, sulfhydryl, acyl and formyl. Where an alkyl group is substituted by an aryl group, this is sometimes referred to as an aralkyl group (e.g. benzyl or substituted benzyl). Typically, aralkyl groups comprise a $C_{1-6}$ alkyl group substituted by an optionally substituted aryl group.

Except where otherwise specified or the context dictates otherwise, by aryl is meant herein a radical formed formally by abstraction of a hydrogen atom from an aromatic compound. Aryl groups are typically monocyclic groups, for example phenyl, although bicyclic aryl groups, such as naphthyl, and tricyclic aryl groups, such as phenanthrene and anthracene, are also embraced by the term aryl. As known to those skilled in the art, heteroaromatic moieties are a subset of aromatic moieties that comprise one or more heteroatoms, typically O, N or S, in place of one or more carbon atoms and optionally any hydrogen atoms attached thereto. Consequentially, it will be understood that heteroaryl groups are a subset of aryl groups. Illustrative heteroaromatic moieties include pyridine, furan, pyrrole and pyrimidine. Further examples of heteroaromatic rings include pyridazine (in which two nitrogen atoms are adjacent in an aromatic 6-membered ring); pyrazine (in which two nitrogens are 1,4-disposed in a 6-membered aromatic ring); pyrimidine (in which two nitrogen atoms are 1,3-disposed in a 6-membered aromatic ring); or 1,3,5-triazine (in which three nitrogen atoms are 1,3,5-disposed in a 6-membered aromatic ring).

Aryl groups may be substituted one or more times with substituents selected from, for example, the group consisting of hydroxy, amino, halo, alkyl, aryl, (including heteroaryl), nitro, alkoxy, alkylthio, cyano, sulfhydryl, acyl and formyl.

DESCRIPTION OF SOME PREFERRED EMBODIMENTS AND EXPERIMENTAL RESULTS

All reagents, reactants and solvents were used as purchased. Anhydrous tetrahydrofuran was collected from a solvent purification system. Flash column chromatography was performed on silica gel 60 Å pore diameter and 40-63 μm particles size. $^1H$ and $^{13}C$ Nuclear Magnetic Resonance (NMR) spectra were recorded on a Bruker-400 MHz or 300 MHz spectrometer at ambient temperature in CDCl3 without TMSCl as internal standard. NMR peaks were assigned by using COSY and HSQC experiments. Elemental analyses were performed at London Metropolitan University 166-220 Holloway Road, London, N7 8DB. High resolution mass spectrometry was performed by the EPSRC National Mass Spectrometry Service Centre (NMSSC), Grove Building Extn., Swansea University, Singleton Park, Swansea, SA2 8PP, UK.

2-Nitroisophthalic Acid XIII $KMnO_4$ (643 g, 4.07 mol, 4.0 eq) was added to solution of NaOH (135 g, 3.38 mol, 3.3 eq) in tap water (4080 mL) at room temperature. 2-Nitro-m-xylene XII (153 g, 1.01 mol, 1.0 eq) was added and the resulting solution was allowed to stir vigorously under strong reflux. The purple colour slowly disappeared as the $KMnO_4$ was reduced and the reaction was continued overnight (12 h). The suspension was cooled to room temperature before being filtered through a sintered funnel. The resulting yellow filtrate was carefully acidified below pH 2 with concentrated sulphuric acid (98%, 200 mL). The white solid formed was collected by filtration and washed with dichloromethane to recover the pure unreacted starting material (31.9 g) after evaporation. The crude white cake was washed with ethyl acetate and filtered. The insoluble white solid was discarded and the resulting filtrate was dried over anhydrous magnesium sulphate. Evaporation of the solvents in vaccuo provided the pure diacid XIII as a white powder (112 g, 52%) and was taken on crude to the next step. (CAS 21161-11-5)

Dimethyl 2-Nitroisophtalate XIV (where $R^1$ is Methyl)

The diacid XIII (136 g, 0.64 mol, 1.0 eq) was diluted in regular methanol (1200 mL) and the resulting solution was carefully treated with concentrated sulphuric acid (98%, 122 mL, 2.24 mol, 3.5 eq). The mixture was allowed to stir overnight under strong reflux and stirring. A large quantity of white solid formed and the condenser was removed to allow half of the methanol to evaporate. The suspension was cooled down to room temperature and was diluted with water (1200 mL) to precipitate more solid. The solid was isolated by filtration and washed with water (1200 mL) before being dissolved in dichloromethane. The solution was dried over anhydrous magnesium sulphate and the solvents were evaporated to give the pure diester 3 (130 g, 84%) as a white powder. (CAS 57052-99-0)

Dimethyl 2-aminoisophtalate X (where $R^1$ is Methyl)

A stream of hydrogen was bubbled through a solution of nitroarene XIV (130 g, 544 mmol, 1.0 eq) and Pd/C (10%, dry, 7.95 g, 6.31 mmol, 1.2 mol %) in regular ethyl acetate (1450 mL) at room temperature. Completion was obtained within 20 h as indicated by TLC analysis. However the reaction time greatly varied depending on the scale and conditions used. The mixture was filtered through a sintered funnel and Pd/C was recovered and successfully reused in other hydrogenations. In the case where wet Pd/C was used, the filtrate was first dried over anhydrous sodium sulphate. The solvents were removed under vacuum to give the desired aniline X (where $R^1$ is methyl) (113 g, 99%) in excellent purity and as a smelly off-white powder. (CAS 57053-02-3)

General Procedure for Grignard Reaction

A solution of alkylmagnesium bromide was prepared under strictly anhydrous conditions from commercially available magnesium and alkylbromide as followed. A suspension of fresh magnesium (9 eq) in anhydrous THF was treated with the slow addition of a premade solution of alkylbromide (8 eq) in anhydrous THF over 1 h in maintaining the temperature below 40 C. After 2 h at room temperature, the suspension was cooled down to 0° C. and a solution of diester (1 eq) in THF was cannulated at 0° C. The reaction was allowed to warm up to room temperature and was stirred until completion as indicated by TLC analysis (<1 h). The reaction was then cooled down to 0 C and carefully quenched with sat. $NH_4Cl$ solution and diluted in $Et_2O$. The organic layer was washed with sat. $NH_4Cl$ solution then dried over anhydrous magnesium sulphate and concentrated under vacuum. The resulting crude oil was generally obtained in excellent purity and no further purification was required.

2,6-Di(3-hydroxypentan-3-yl)aniline XIa ($R^2$=Me)

A solution of ethylmagnesium bromide was prepared under strictly anhydrous conditions from commercially available magnesium and ethylbromide. A suspension of fresh magnesium (105 g, 4.33 mol, 9.0 eq) in anhydrous THF (1700 mL) was treated with the slow addition of a premade solution of ethylbromide (285 mL, 3.82 mol, 8.0 eq) in anhydrous THF (1700 mL) over 1 h in maintaining the temperature below 40° C. After 2 h at room temperature, the suspension was cooled down to 0° C., causing the formation of a precipitate, and the diester X (where $R^1$ is methyl) (100 g, 0.48 mol, 1.0 eq) was carefully added portionwise over 5 min at 0° C. The reaction was allowed to warm up to room temperature and was stirred until completion as indicated by TLC analysis (<1 h). The reaction was then cooled down to 0° C. and carefully quenched with sat. $NH_4Cl$ solution (500 mL). The mixture was diluted in $Et_2O$ (1700 mL) and washed with sat. $NH_4Cl$ solution (2×500 mL). The organic layer was then dried over anhydrous magnesium sulphate and concentrated under vacuum. The resulting crude oil was then filtered thru a pad of silica and flushed with $Et_2O$ to get a more accurate yield. Evaporation of the solvent provided the crude diol XIa (116 g, 91%) as a yellow/greenish oil in excellent purity. No further purification was required for the next steps.

$^1$H NMR (400 MHz, $CDCl_3$) δ 0.84 (12H, app t, J=7.4 Hz, 4×$CH_3$), 1.92 (4H, m, 4×CH), 2.05 (4H, m, 4×CH), 4.26 (2H, vbs, $NH_2$), 6.57 (1H, t, J=7.7 Hz, $H^{p\text{-}Ar}$), 6.92 (2H, d, J=7.7 Hz, $H^{m\text{-}Ar}$).

$^{13}$C {$^1$H} NMR (100 MHz, $CDCl_3$) δ 8.3 (4×$CH_3$), 30.8 (4×$CH_2$), 79.9 (2×$C_{IV}$—OH), 115.4 ($CH^{p\text{-}Ar}$), 126.8 (2×$CH^{m\text{-}Ar}$), 128.2 (2×$CH^{o\text{-}Ar}$), 146.7 ($C_{IV}^{Ar}$—$NH_2$). HRMS (NSI+). found m/z [M+H]+266.2115, calcd for $C_{16}H_{28}NO_2$ 266.2115.

2,6-Di(4-hydroxyheptan-4-yl)aniline XIb ($R^2$=Et)

A suspension of fresh magnesium (20.9 g, 0.86 mol, 8.6 eq) in anhydrous THF (300 mL) was treated with the slow addition of a premade solution of n-propylbromide (69.5 mL, 0.77 mol, 7.7 eq) in anhydrous THF (300 mL) over 20 min in maintaining the temperature below 40° C. After 1.5 h at room temperature, the suspension was cooled down to 0° C., causing the formation of a precipitate, and a premade solution of diester X (where $R^1$ is methyl) (20.0 g, 0.10 mol, 1.0 eq) in dry THF (300 mL) was cannulated at 0° C. The reaction was allowed to warm up to room temperature and was stirred for 2 h. The reaction was then cooled down to 0° C. and carefully quenched with sat. $NH_4Cl$ solution (300 mL). The mixture was diluted in $Et_2O$ (400 mL) and washed with sat. $NH_4Cl$ solution (2×200 mL). The organic layer was then dried over anhydrous magnesium sulphate and concentrated under vacuum. The resulting brown crude solid (30.9 g) (Pure by $^1$H NMR) was then further purified by successive recrystallisation from pentane to give the pure diol XIb (26.6 g, 86%) as a white crystalline solid.

$^1$H NMR (400 MHz, $CDCl_3$) δ 0.90 (12H, app t, J=7.3 Hz, 4×$CH_3$), 1.08-1.23 (4H, m, 4×CH), 1.26-1.41 (4H, m, 4×CH), 1.78-1.88 (4H, td, J=12.5, 4.5 Hz, 4×CH), 1.95-2.05 (4H, td, J=12.5, 4.5 Hz, 4×CH), 4.24 (3H, vbs, $NH_2$+2×OH), 6.54 (1H, t, J=7.7 Hz, $H^{p\text{-}Ar}$), 6.89 (2H, d, J=7.7 Hz, $H^{m\text{-}Ar}$).

$^{13}$C {$^1$H} NMR (100 MHz, $CDCl_3$) δ 14.5 (4×$CH_3$), 17.2 (4×$CH_2$), 41.2 (4×$CH_2$), 79.4 (2×$C_{IV}$—OH), 115.1 ($CH^{p\text{-}Ar}$), 126.5 (2×$CH^{m\text{-}Ar}$), 128.7 (2×$CH^{o\text{-}Ar}$), 146.7 ($C_{IV}^{Ar}$—$NH_2$). HRMS (NSI+). found m/z [M+H]+322.2745, calcd for $C_{20}H_{36}O_2N$, 322.2741.

2,6-Di(5-hydroxynonan-5-yl)aniline XIc ($R^2$=n-Pr)

A solution of n-butylmagnesium bromide was prepared under strictly anhydrous conditions from commercially available magnesium and n-butylbromide as followed. A suspension of fresh magnesium (16.0 g, 0.66 mol, 9.4 eq) in anhydrous THF (200 mL) was treated with the slow addition of a premade solution of n-butylbromide (58.0 mL, 0.54 mol, 7.7 eq) in anhydrous THF (200 mL) over 1 h in maintaining the temperature below 40° C. After 2 h at room temperature, the suspension was cooled down to 0° C., causing the formation of a precipitate, and a solution of diester X (where $R^1$ is methyl) (14.0 g, 0.07 mol, 1.0 eq) in dry THF (200 mL) was cannulated at 0° C. The reaction was allowed to warm up to room temperature and was stirred until completion as indicated by TLC analysis (<1 h). The reaction was then cooled down to 0° C. and carefully quenched with sat. $NH_4Cl$ solution (200 mL). The mixture was diluted in $Et_2O$ (250 mL) and washed with sat. $NH_4Cl$ solution (2×150 mL). The organic layer was then dried over anhydrous magnesium sulphate and concentrated under vacuum. The resulting brownish crude solid (pure by $^1$H NMR) was then recrystallized from hot pentane to give the pure diol XIc (24.4 g, 97%) as an off-white crystalline solid.

$^1$H NMR (400 MHz, $CDCl_3$) δ 0.88 (12H, app t, J=7.2 Hz, 4×$CH_3$), 1.14 (4H, m, 4×CH), 1.32 (12H, m, 12×CH), 1.87 (4H, m, 4×CH), 2.03 (4H, m, 4×CH), 2.24 (2H, partially hidden vbs, 2×OH), 5.98 (2H, vbs, $NH_2$), 6.56 (1H, t, J=7.9 Hz, $H^{p\text{-}Ar}$), 6.91 (2H, d, J=7.9 Hz, $H^{m\text{-}Ar}$).

$^{13}$C {$^1$H} NMR (100 MHz, $CDCl_3$) δ 14.0 (4×$CH_3$), 23.1 (4×$CH_2$), 26.1 (4×$CH_2$), 38.1 (4×$CH_2$), 79.3 (2×$C_{IV}$—OH), 115.0 ($CH^{p\text{-}Ar}$), 126.5 (2×$CH^{m\text{-}Ar}$), 128.4 (2×$CH^{o\text{-}Ar}$), 146.7 ($C_{IV}^{Ar}$—$NH_2$).

HRMS (NSI+). found m/z [M+H]+378.3369, calcd for $C_{24}H_{44}NO_2$ 378.3367.

General Procedure for Diol Dehydration and Dialkene Hydrogenation

A solution of diol (1.0 eq) in regular THF was treated with the careful addition of conc. sulphuric acid (98%, 10 eq) and stirred at 100° C. in an open vessel. After 1-2 h at 100° C. most of the THF evaporated and completion was observed by TLC analysis of a worked up crude sample. The reaction was cooled down to room temperature and was carefully poured into a separating funnel containing a saturated aqueous solution of sodium hydroxide. The basic mixture was then extracted with diethyl ether and the combined extracts were dried over anhydrous magnesium sulphate. Filtration followed by concentration of the organic extracts under vacuum gave the crude dialkene as a brownish viscous oil. The crude dialkene was obtained in excellent purity as a variable mixture of (E)- and (Z)-double bond isomers and was used without any further purification in the next step.

Pd/C (10 mol %) was added to a solution of crude dialkene (1.0 eq) in regular ethanol. The reaction was then purged under vacuum then nitrogen and was finally placed under positive pressure of hydrogen. The mixture was allowed to reflux until completion as indicated by $^1$H NMR. The reaction time required to reach completion varied (6 to 48 h) depending on the substrate, the scale and the conditions used. The mixture was filtered through a sintered funnel and the recovered Pd/C was efficiently reused for larger scale reactions. The yellow filtrate was concentrated under vacuum to afford the desired aniline as a light yellow to brown oil. Excellent purity was obtained and the crude oil was generally used without any further purification. However filtration through a pad of silica and flushing with pentane/$Et_2O$ can be used to get rid of coloured impurities and traces of Pd/C.

2,6-Di(pentan-3-yl)aniline Ia ($R^2$=Me)

A solution of dial (2.72 g, 10.2 mmol, 1.0 eq) in regular THF (100 mL) was treated with the careful addition of conc. sulphuric acid (98%, 5.50 mL, 101 mmol, 9.9 eq) and stirred at 100° C. in an open vessel. After 2 h at 100 C most of the THF evaporated and completion was observed by TLC analysis of a worked up crude sample. The reaction was cooled down to room temperature and was carefully poured into a separating funnel containing a saturated aqueous solution of sodium hydroxide (12 mL). The basic mixture was then extracted with diethyl ether (3×100 mL) and the combined extracts were dried over anhydrous magnesium sulphate. Filtration followed by concentration of the organic extracts under vacuum gave the crude dialkene (2.31 g, 98%) as a brownish viscous oil in excellent purity.

Pd/C (10%, 59.6% wet, 1.84 g, 1.03 mmol, 10 mol %) was added to a solution of crude dialkene (2.31 g, ~10.2 mmol, 1.0 eq) in regular ethanol (50 mL). The mixture was allowed to reflux under a positive pressure of hydrogen until completion (48 h) and was filtered through a sintered funnel. The yellow filtrate was concentrated under vacuum to afford the desired aniline Ia (2.00 g, 84% over 2 steps) as a light yellow to brown oil in excellent purity. (KS19) On larger scale (>80 g) the aniline was purified by distillation under reduced pressure as described in the literature. Distillation afforded the pure aniline Ia as a slightly yellowish oil (7 mbar, by 140° C.). However slight decomposition was observed during distillation and prolonged storage at room temperature. The data obtained are in full agreement with those from the literature.

1H NMR (400 MHz, $CDCl_3$) δ 0.88 (12H, 2×t, J=2×7.5 Hz, 4×$CH_3$), 1.65 (4H, m, 2×$CH_2$), 1.75 (4H, m, 2×$CH_2$), 2.53 (2H, m, 2×CH), 3.62 (23H, vbs, $NH_2$), 6.82 (1H, t, J=7.4 Hz, $H^{p-Ar}$), 6.95 (2H, d, J=7.4 Hz, $H^{m-Ar}$).

$^{13}C$ {$^1H$} NMR (100 MHz, $CDCl_3$) δ 12.0 (4×$CH_3$), 28.0 (4×$CH_2$), 42.3 (2×CH), 118.4 ($CH^{p-Ar}$), 123.8 (2×$CH^{m-Ar}$), 129.9 (2×$C_{IV}^{o-Ar}$), 142.5 (2×N—$C_{IV}^{Ar}$).

2,6-Di(heptan-4-yl)aniline Ib ($R^2$=Et)

A solution of diol (25.9 g, 80.6 mmol, 1.0 eq) in regular THE (200 mL) was treated with the careful addition of conc. sulphuric acid (98%, 43.0 mL, 790 mmol, 9.8 eq) and stirred at 100° C. in an open vessel. After 2 h at 100° C. most of the THF evaporated and completion was observed by TLC analysis of a worked up crude sample. The reaction was cooled down to room temperature and was carefully poured into a separating funnel containing a saturated aqueous solution of sodium hydroxide (90 mL). The basic mixture was then extracted with diethyl ether (3×500 mL) and the combined extracts were dried over anhydrous magnesium sulphate. Filtration followed by concentration of the organic extracts under vacuum gave the crude dialkene (22.7 g, 99%) as a viscous light yellow oil in excellent purity.

Pd/C (~10%, recycled, 30.0 g, ~28.2 mmol, ~35 mol %) was added to a solution of crude dialkene (22.7 g, ~80.6 mmol, 1.0 eq) in regular ethanol (600 mL). The mixture was allowed to reflux under a positive pressure of hydrogen until completion (3.5 h) and was filtered through a sintered funnel. The yellow filtrate was concentrated under vacuum to afford the desired aniline Ib (21.1 g, 91% over 2 steps) as a light yellow oil in excellent purity.

$^1H$ NMR (400 MHz, $CDCl_3$) δ 0.87 (12H, app t, J=7.3 Hz, 4×$CH_3$), 1.21-1.31 (8H, m, 4×$CH_2$), 1.52-1.68 (8H, m, 4×$CH_2$), 2.66 (2H, m, 2×CH), 3.66 (2H, vbs, $NH_2$), 6.77 (1H, t, J=7.5 Hz, $H^{p-Ar}$), 6.92 (2H, d, J=7.5 Hz, $H^{m-Ar}$).

$^{13}C$ {$^1H$} NMR (100 MHz, $CDCl_3$, SEM233) δ 14.5 (4×$CH_3$), 17.2 (4×$CH_2$), 41.2 (4×$CH_2$), 79.4 (2×$C_{IV}$—OH), 115.1 ($CH^{p-Ar}$), 126.5 (2×$CH^{m-Ar}$), 128.7 (2×$CH^{o-Ar}$), 146.7 ($C_{IV}^{Ar}$—$NH_2$).

HRMS (NSI+). found m/z [M+H]+290.2847, calcd for $C_{20}H_{36}N$, 290.2842.

2,6-Di(nonan-5-yl)aniline Ic ($R^2$=n-Pr)

A solution of diol (10.1 g, 26.7 mmol, 1.0 eq) in regular THF (230 mL) was treated with the careful addition of conc. sulphuric acid (98%, 14.3 mL, 263 mmol, 9.9 eq) and stirred at 100° C. in an open vessel. After 1 h at 100° C. most of the THF evaporated and completion was observed by TLC analysis of a worked up crude sample. The reaction was cooled down to room temperature and was carefully poured into a separating funnel containing a saturated aqueous solution of sodium hydroxide (42 mL). The basic mixture was then extracted with diethyl ether (3×250 mL) and the combined extracts were dried over anhydrous magnesium sulphate. Filtration followed by concentration of the organic extracts under vacuum gave the crude dialkene (10.2 g) as a yellowish clear viscous oil in excellent purity.

Pd/C (10% dry, 3.21 g, 3.02 mmol, 11 mol %) was added to a solution of crude dialkene (10.2 g, ~26.7 mmol, 1.0 eq) in regular ethanol (150 mL). The mixture was allowed to reflux under a positive pressure of hydrogen until completion (19 h) and was filtered through a sintered funnel. The yellow filtrate was concentrated under vacuum to afford the desired aniline Ic (8.05 g, 87% over 2 steps) as a clear yellow to orange oil in excellent purity.

$^1H$ NMR (400 MHz, $CDCl_3$) δ 0.88 (12H, app t, J=7.0 Hz, 4×$CH_3$), 1.28 (16H, m, 8×$CH_2$), 1.65 (8H, m, 4×$CH_2$), 2.65 (2H, m or bs, 2×CH), 3.65 (2H, bs, $NH_2$), 6.80 (1H, m, $H^{p-Ar}$), 6.95 (2H, d, J=7.2 Hz, $H^{m-Ar}$).

$^{13}C$ {$^1H$} NMR (100 MHz, $CDCl_3$) δ 14.0 (4×$CH_3$), 23.0 (4×$CH_2$), 29.8 (4×$CH_2$), 35.7 (4×$CH_2$), 39.0 (2×CH), 118.4 ($CH^{p-Ar}$), 123.7 (2×$CH^{m-Ar}$), 130.6 (2×$CH^{o-Ar}$), 142.1 ($C_{IV}^{Ar}$—$NH_2$).

HRMS (NSI+). found m/z [M+H]+346.3474, calcd for $C_{24}H_{44}N$, 378.346.3468.

General Procedure for Diimine Preparation

A stirred solution of aniline (2.0 eq) in regular methanol was treated with glyoxal (40% in $H_2O$, 1.2 eq) followed by catalytic amount of formic acid (0.3 eq) at room temperature. The desired diimine started to precipitate from the reaction media and stirring was continued until completion as indicated by $^1H$ NMR analysis. The pure diimine was successfully obtained by either recrystallization of the crude from methanol or ethanol or by filtration through a pad of silica.

The spontaneous crystallisation of the diimine at the end of the reaction can be increased by ceasing the stirring after 15 min, and leaving the reaction mixture overnight or placing the reaction mixture in the freezer. The reaction can also be done in ethanol but spontaneous crystallisation of the diimine at the end of the reaction was not as efficient as in methanol. Residual diimine obtained by concentration of the filtrate can also be purified successfully by filtration through silica gel and flushing (eluting) with pentane.

N,N'-Bis[2,6-di(pentan-3-yl)phenyl]diazabutadiene IIa ($R^2$=Me)

A stirred solution of IPent aniline (Ia) (18.3 g, 78.6 mmol, 2.0 eq) in regular methanol (230 mL) was treated with glyoxal (40% in H$_2$O, 5.40 mL, 49.1 mmol, 1.3 eq) followed by catalytic amount of formic acid (460 µL, 12.2 mmol, 0.3 eq) at room temperature. The desired diimine started to precipitate from the reaction media and stirring was continued until completion (3 h). The solid was isolated by filtration and the filtrate was concentrated under vacuum. The resulting brownish solid was recrystallized from methanol. Both solids were combined and dried under high vacuum to afford the pure desired diimine IIa as a bright and shiny yellow crystalline powder (16.0 g, 83%).

$^1$H NMR (400 MHz, CDCl$_3$) δ 0.82 (24H, t, J=7.3 Hz, 8×CH$_3$), 1.59 (8H, m, 4×CH$_2$), 1.68 (8H, m, 4×CH$_2$), 2.52 (4H, m, 4×CH), 7.08-7.10 (4H, m, 4×H$^{m\text{-}Ar}$), 7.14-7.18 (2H, m, 2×H$^{p\text{-}Ar}$), 8.04 (2H, s, 2×HC=N).

$^{13}$C {$^1$H} NMR (100 MHz, CDCl$_3$) δ 12.2 (8×CH$_3$), 28.9 (8×CH$_2$), 42.5 (4×CH), 123.9 (4×CH$^{m\text{-}Ar}$), 124.8 (2×CH$^{p\text{-}Ar}$), 133.8 (4×C$_{IV}^{o\text{-}Ar}$), 150.9 (2×N—C$_{IV}^{Ar}$), 163.9 (2×HC=N).

HRMS (NSI+). found m/z [M+H]+489.4199, calcd for C$_{34}$H$_{53}$N$_2$ 489.4203.

N,N'-Bis [2,6-di(heptan-4-yl)phenyl]diazabutadiene IIb (R$^2$=Et)

A stirred solution of IHept aniline (Ib) (20.6 g, 71.2 mmol, 2.0 eq) in regular methanol (210 mL) was treated with glyoxal (40% in H$_2$O, 4.88 mL, 44.4 mmol, 1.2 eq) followed by catalytic amount of formic acid (420 µL, mmol, 0.3 eq) at room temperature. The desired diimine started to precipitate from the reaction media and stirring was continued until completion (5 h). The solid was isolated by filtration and the filtrate was concentrated under vacuum. The resulting brownish solid was filtered through a plug of silica and flushed with pentane. After concentration, both solids were combined and dried under high vacuum to afford the pure desired diimine IIb as a bright and shiny yellow crystalline powder (19.1 g, 89%).

$^1$H NMR (400 MHz, CDCl$_3$) δ 0.88 (24H, app t, J=7.4 Hz, 8×CH$_3$), 1.24 (16H, m, 8×CH$_2$), 1.59 (16H, m, 8×CH$_2$), 2.74 (4H, m, 4×CH), 7.12-7.19 (6H, m, H$^{Ar}$), 8.05 (2H, s, 2×CH=N).

$^{13}$C {$^1$H} NMR (100 MHz, CDCl$_3$) δ 14.3 (4×CH$_3$), 20.8 (4×CH$_2$), 38.4 (4×CH), 39.1 (4×CH$_2$), 123.8 (CH$^{p\text{-}Ar}$), 124.8 (2×CH$^{m\text{-}Ar}$), 134.3 (2×CH$^{o\text{-}Ar}$), 150.6 (C$_{IV}^{Ar}$—NH$_2$), 163.8 (CH=N).

HRMS (APCI+). found m/z [M+H]+601.5453, calcd for C$_{42}$H$_{69}$N$_2$ 601.5455.

N,N'-Bis [2,6-di(nonan-5-yl)phenyl]diazabutadiene IIc (R$^2$=n-Pr)

A stirred solution of INon aniline (Ic) (1.43 g, 4.14 mmol, 2.0 eq) in regular methanol (12 mL) was treated with glyoxal (40% in H$_2$O, 284 µL, 2.48 mmol, 1.2 eq) followed by catalytic amount of formic acid (24 µL, mmol, 0.3 eq) at room temperature. The desired diimine started to precipitate from the reaction media and stirring was continued until completion (4 h). The methanol was evaporated under vacuum and the residue was diluted in pentane (12 mL) then dried over anhydrous sodium sulfate. The filtrate was passed through a short pad of silica and flushed with pentane. The pentane was evaporated under vacuum and the remaining yellow solid was recrystallized from ethanol. The pure desired diimine IIc was obtained as a bright and shiny yellow crystalline powder (1.02 g, 69%).

$^1$H NMR (400 MHz, CDCl$_3$) δ 0.85 (24H, app t, J=7.2 Hz, 4×CH$_3$), 1.13-1.33 (32H, m, 16×CH$_2$), 1.53-1.66 (16H, m, 8×CH$_2$), 2.68 (4H, m, 4×CH), 7.11 (4H, d, J=6.8 Hz, H$^{m\text{-}Ar}$), 7.16 (2H, t, J=6.8 Hz, H$^{m\text{-}Ar}$), 8.00 (2H, s, 2×CH=N).

$^{13}$C {$^1$H} NMR (100 MHz, CDCl$_3$) δ 14.0 (8×CH$_3$), 22.9 (8×CH$_2$), 29.9 (8×CH$_2$), 36.6 (8×CH$_2$), 38.9 (4×CH), 123.8 (2×CH$^{p\text{-}Ar}$), 124.8 (4×CH$^{m\text{-}Ar}$), 134.4 (4×CH$^{o\text{-}Ar}$), 150.7 (2×C$_{IV}^{Ar}$—NH$_2$), 163.6 (2×CH=N).

HRMS (APCI+). found m/z [M+H]+713.6711, calcd for C$_{50}$H$_{85}$N$_2$ 713.6707.

General Procedure for Imidazolium Chloride Preparation

A solution of diimine (1.0 eq) in regular THF was treated with anhydrous zinc chloride (1.0 eq) at 70° C. and stirred for 5 min. para-formaldehyde (1.1 eq) was subsequently added followed by the dropwise addition of anhydrous HCl (4.0 M in dioxane, 1.5 eq). The reaction was stirred for 3 h at 70° C. and concentrated down under vacuum. The residue was dissolved in ethyl acetate and was washed with water and brine. The combined aqueous phases were extracted with ethyl acetate and the organic phases were combined and dried over anhydrous magnesium sulphate. The solvent was partially evaporated under vacuum until the formation of a solid and the resulting suspension was diluted with pentane and placed in the freezer for 20 min. The solid was isolated by filtration and washed with pentane to afford the pure desired imidazolium chloride as an off-white crystalline powder.

In general it was found that crystallization of the crude imidazolinium salts is improved by work up procedures such as that described above, including extraction into ethyl acetate and/or brine washes after reaction.

1,3-Bis[2,6-di(pentan-3-yl)phenyl]imidazolium chloride IIIa (R$^2$=Me, IPent.HCl)

A solution of IPent diimine IIa (3.00 g, 6.14 mmol, 1.0 eq) in regular tetrahydrofuran (240 mL) was treated with anhydrous zinc chloride (837 mg, 6.14 mmol, 1.0 eq) at 70° C. and stirred for 5 min. p-formaldehyde (193 mg, 6.43 mmol, 1.1 eq) was subsequently added followed by the dropwise addition of anhydrous HCl (4.0 M in dioxane, 2.3 mL, 9.1 mmol, 1.5 eq). The reaction was stirred for 3 h at 70° C. and concentrated down under vacuum. The residue was dissolved in ethyl acetate (200 mL) and was washed with water (3×200 mL) and brine (200 mL). The combined aqueous phases were extracted with ethyl acetate (200 mL) and the organic phases were combined and dried over anhydrous magnesium sulphate. The solvent was partially evaporated under vacuum until the apparition of a solid and the resulting suspension was diluted with pentane and placed in the freezer for 20 min. The solid was isolated by filtration and washed with pentane to afford the pure desired imidazolium chloride IIIa as an off-white crystalline powder (2.36 g, 71%).

$^1$H NMR (400 MHz, CDCl$_3$) δ 0.78 (12H, t, J=7.4 Hz, 4×CH$_3$), 0.86 (12H, t, J=7.4 Hz, 4×CH$_3$), 1.68 (16H, m, 8×CH$_2$), 1.96 (4H, m, 4×CH), 7.29 (4H, d, J=7.9 Hz, 4×H$^{m\text{-}Ar}$), 7.61 (2H, t, J=7.9 Hz, 2×H$^{p\text{-}Ar}$), 8.32 (2H, app d, J=1.7 Hz, 2×HC=N), 8.87 (1H, bs, N—CH—N).

$^{13}$C {$^1$H} NMR (100 MHz, CDCl$_3$) δ 11.9 (4×CH$_3$), 12.1 (4×CH$_3$), 28.0 (4×CH$_2$), 28.7 (4×CH$_2$), 43.1 (4×CH), 125.0 (4×CH$^{m\text{-}Ar}$), 127.5 (2×CH=N), 131.8 (2×CH$^{p\text{-}Ar}$), 132.1 (4×C$_{IV}^{o\text{-}Ar}$) or 135.9 (N—CH—N), 142.0 (2×N—C$_{IV}^{Ar}$).

Anal. Calcd for C$_{35}$H$_{53}$ClN$_2$: C, 78.24; H, 9.94; N, 5.21. Found: C, 78.13; H, 10.03; N, 5.19.

1,3-Bis [2,6-di(heptan-4-yl)phenyl]imidazolium chloride IIIb (R²=Et, IHept.HCl)

A solution of diimine (19.1 g, 31.8 mmol, 1.0 eq) in regular tetrahydrofuran (1500 mL) was treated with anhydrous zinc chloride (4.33 g, 31.8 mmol, 1.0 eq) at 70° C. and stirred for 5 min. p-formaldehyde (1.00 g, 33.4 mmol, 1.1 eq) was subsequently added followed by the dropwise addition of anhydrous HCl (4.0 M in dioxane, 11.8 mL, 47.72 mmol, 1.5 eq). The reaction was stirred for 3 h at 70° C. and concentrated down under vacuum. The residue was dissolved in ethyl acetate (1000 mL) and was washed with water (2×750 mL) and brine (750 mL). The combined aqueous phases were extracted with ethyl acetate (200 mL) and the organic phases were combined and dried over anhydrous magnesium sulphate. The solvent was partially evaporated under vacuum until the formation of a solid and the resulting suspension was diluted with pentane and placed in the freezer for 20 min. The solid was isolated by filtration and washed with pentane to afford the pure desired imidazolium chloride IIIb as a white crystalline powder (9.72 g, 47%).

$^1$H NMR (400 MHz, CDCl$_3$) δ 0.84 (12H, t, J=7.2 Hz, 4×CH$_3$), 0.87 (12H, t, J=7.2 Hz, 4×CH$_3$), 0.97-1.14 (12H, m, 4×CH+4 CH$_2$), 1.27 (4H, m, 4×CH), 1.49-1.69 (16H, m, 4×CH$_2$+4×CH$_2$), 2.05 (4H, sharp m, 4 CH+impurity), 7.29 (4H, d, J=7.8 Hz, H$^{m-Ar}$), 7.60 (2H, t, J=7.8 Hz, H$^{p-Ar}$), 8.20 (1H, s, N—CH—N), 8.41 (2H, s, 2×CH=N).

$^{13}$C {$^1$H} NMR (100 MHz, CDCl$_3$) δ 13.8 (4×CH$_3$), 14.1 (4×CH$_3$), 20.6 (4×CH$_2$), 21.0 (4×CH$_2$), 37.9 (4×CH), 39.1 (4×CH$_2$), 40.3 (4×CH), 125.0 (CH$^{m-Ar}$), 127.7 (2×HC=N), 131.4 (2×C$_{IV}^{o-Ar}$), 132.0 (2×CH$^{p-Ar}$), 134.9 (N—CH—N), 142.5 (N—C$_{IV}^{Ar}$).

Anal. Calcd for C$_{43}$H$_{69}$ClN$_2$: C, 79.52; H, 10.71; N, 4.31. Found: C, 79.39; H, 10.72; N, 4.35.

1,3-Bis [2,6-di(nonan-5-yl)phenyl]imidazolium chloride IIIc (R²=n-Pr, INon.HCl)

A solution of diimine IIc (685 mg, 0.96 mmol, 1.0 eq) in regular tetrahydrofuran (35 mL) was treated with anhydrous zinc chloride (131 mg, 0.96 mmol, 1.0 eq) at 70° C. and stirred for 5 min. p-formaldehyde (30.0 mg, 1.00 mmol, 1.0 eq) was subsequently added followed by the dropwise addition of anhydrous HCl (4.0 M in dioxane, 355 L, 1.42 mmol, 1.5 eq). The reaction was stirred for 3 h at 70° C. and concentrated down under vacuum. The residue was dissolved in ethyl acetate (30 mL) and was washed with water (3×20 mL) and brine (20 mL). The combined aqueous phases were extracted with ethyl acetate (10 mL) and the organic phases were combined and dried over anhydrous magnesium sulphate. The solvent was completely evaporated under vacuum and the resulting solid was washed with pentane to afford the pure desired imidazolium chloride IIIc as a white crystalline powder (262 mg, 36%).

$^1$H NMR (400 MHz, CDCl$_3$) δ 0.81 (12H, t, J=7.2 Hz, 4×CH$_3$), 0.88 (12H, t, J=7.2 Hz, 4×CH$_3$), 0.96-1.10 (12H, m, 4×CH+4 CH$_2$), 1.18-1.34 (20H, m, 8×CH$_2$+4×CH), 1.51-1.77 (16H, m, 4×CH$_2$+4×CH$_2$), 2.06 (4H, 4 CH), 7.32 (4H, d, J=7.8 Hz, H$^{m-Ar}$), 7.63 (2H, t, J=7.8 Hz, H$^{p-Ar}$), 8.23 (1H, s, N—CH—N), 8.48 (2H, s, 2×CH=N).

$^{13}$C {$^1$H} NMR (100 MHz, CDCl$_3$) δ 13.8 (4×CH$_3$), 13.9 (4×CH$_3$), 22.6 (4×CH$_2$), 22.9 (8×CH$_2$), 30.0 (4×CH$_2$), 30.1 (4×CH$_2$), 35.5 (4×CH$_2$), 36.8 (4×CH$_2$), 40.6 (4×CH), 125.3 (CH$^{m-Ar}$), 128.0 (2×HC=N), 131.7 (2×C$_{IV}^{o-Ar}$), 132.3 (2×CH$^{p-Ar}$), 135.0 (N—CH—N), 142.8 (N—C$_{IV}^{Ar}$).

Anal. Calcd for C$_{51}$H$_{85}$ClN$_2$: C, 80.42; H, 11.25; N, 3.68. Found: C, 80.25; H, 11.12; N, 3.77.

Procedure for the Preparation of Imidazolium Chlorides with Para-Methoxy Substituents p-Iodo Anilines

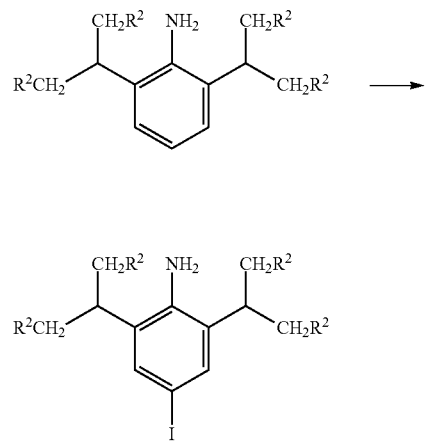

A solution of the aniline in regular cyclohexane was treated with a saturated aqueous solution of Na$_2$CO$_3$ followed by solid iodine at room temperature. The reaction was stirred overnight at room temperature (14 h). The crude solution was diluted in Et$_2$O and washed with a saturated aqueous solution of Na$_2$S$_2$O$_3$. The organic layer was then dried over anhydrous sodium sulphate and concentrated under vacuum. The resulting residue was generally obtained in excellent purity and was either used without further purification or filtered through silica and flushed with 1% Et$_2$O in pentane.

Procedure for p-Iododiimine Preparation

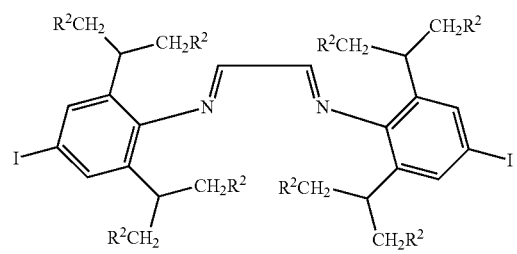

A solution of p-iodo-aniline (2.0 eq) in MeOH was treated with formic acid (1 drop) followed by the dropwise addition of glyoxal (40% in H$_2$O, 1.2 eq) at 70 C. The solution was stirred at this temperature for 3 h and the methanol was evaporated under vacuum and replaced by Et$_2$O. Reaction overnight at room temperature may also be used to affect the transformation. The solution was dried over anhydrous sodium sulphate, filtered and concentrated in vacuuo. The residue was purified by flash column chromatography (silica gel, 1-5% Et$_2$O in pentane) to yield the pure desired diimine as a bright yellow solid. Purification by flash column chromatography was preferred on small scale synthesis to obtain accurate yields. However on larger scale, the pure desired diimines usually precipitated out of the methanolic solution and can be easily isolated by filtration.

Procedure for p-Methoxydiimine Preparation

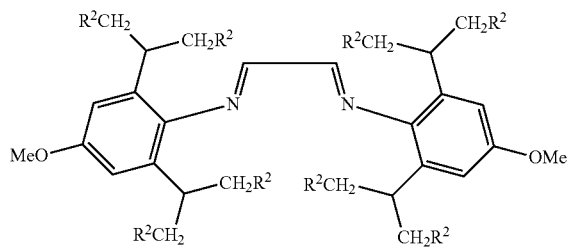

A sealed tube was loaded with regular methanol, CuI (0.5 eq), phenanthroline (0.8 eq) and $Cs_2CO_3$ (4.3 eq) at room temperature. To this brown mixture was added the starting diiodo diimine (1.0 eq) and the reaction was stirred overnight at for example 110 C. The reaction was allowed to cool down to room temperature and was filtered through cotton wool. The remaining solid was washed with diethyl ether and the filtrate was transferred into a separating funnel. The organic layer was washed with 10% $NH_4OH$ then brine and was then dried over anhydrous sodium sulphate. Concentration in vacuuo afforded the crude dimethoxy diimine. Although excellent purity was generally obtained ($^1H$ NMR), filtration through silica was preferred to remove colouring agents and traces of copper. The silica was flushed with pentane and the filtrate was evaporated to yield the pure desired diimine.

Anhydrous conditions are not required. Preliminary results show that completion is actually reached within a few hours. Conditions were not optimised and quantities of reagents may be significantly reduced.

Where the diimine has groups $R^2$=H (isopropyl substituents at the 2 and 6 positions) the expected p-methoxydiimine was not formed but instead the corresponding p-methoxyaniline (below) was produced (73% yield, overnight in a sealed tube reaction at 120 C). The diimine bridge is cleaved in this example. Bulkier $R^2$ groups such as methyl, ethyl and n-propyl produced high yields 100% to 94%) of the methoxydiimines, with little free aniline (3%) indicating a steric effect.

The diisopropyl aniline produced can be readily converted to the corresponding diimine by reacting again with formic acid and glyoxal (40% in $H_2O$) in methanol as shown below.

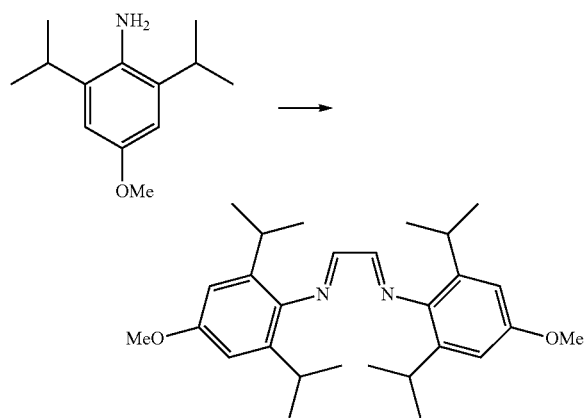

More generally if the p-methoxy anilines are desired the diimine bridge of the p-methoxy diimines can be readily cleaved as shown below. For example reaction with acid such as hydrochloric acid in aqueous solvent (e.g. water/THF) at moderate temperature (e.g. room temperature to 100 C). Reaction may be complete in as little as 20 to 30 minutes. Thus the diimine function can serve as a protecting group when anilines of the invention are desired products.

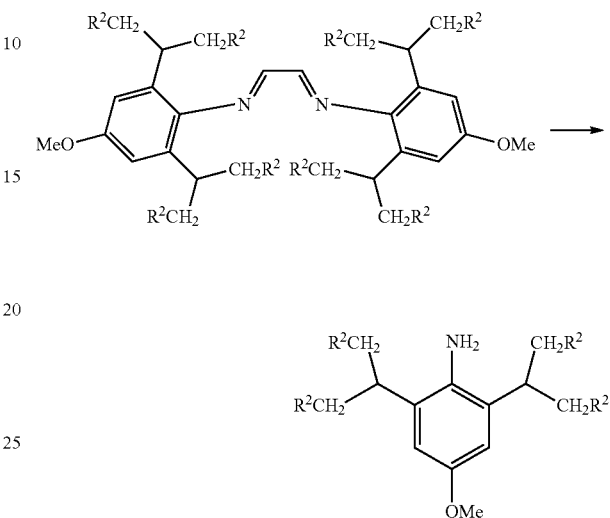

Procedure for p-Methoxyimidazolium Chloride Preparation

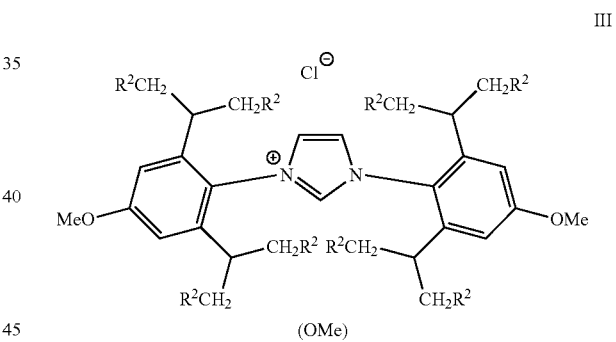

A solution of p-methoxydiimine (1.0 eq) in regular tetrahydrofuran was treated with anhydrous zinc chloride (1.0 eq) at 70° C. and stirred for 5 min. p-formaldehyde (1.1 eq) was subsequently added followed by the dropwise addition of anhydrous HCl (4.0 M in dioxane, 1.5 eq). The reaction was stirred for at 70° C. and concentrated under vacuum. The residue was dissolved in ethyl acetate and was washed with water and brine. The combined aqueous phases were extracted with ethyl acetate and the organic phases were combined and dried over anhydrous magnesium sulphate. The solvent was evaporated under vacuum and the resulting brown solid was triturated with pentane to yield the pure desired imidazolium chloride as the remaining solid.

The above procedure was used to prepare the imidazolium salts: IPr-OMe.HCl IPent-OMe.HCl, IHept-OMe.HCl and INon-OMe.HCl. (The structures III(OMe) above where groups $R^2$ are respectively H, Me, Et, and n-Pr.) These imidazolium salts were used to prepare NHC containing palladium complexes as described below.

Procedure for the Preparation of SIPr-OMe.HCl

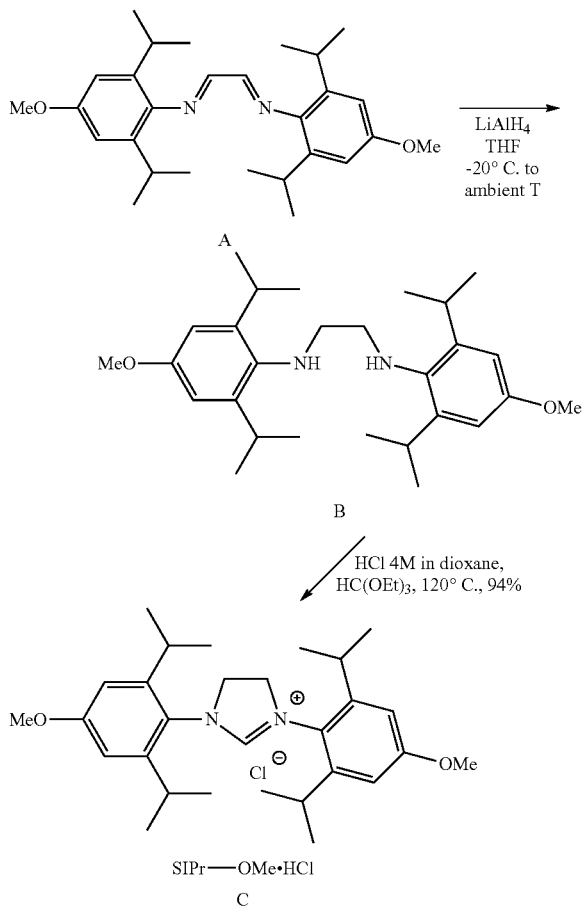

A—

The diimine precursor N,N'-Bis(4-methoxy-2,6-diisopropylphenyl)1,4-diazabutadiene (A) was made by following a variation of the General Procedure for Diimine Preparation discussed above. A solution of 4-methoxy-2,6-diisopropylaniline (15.2 g, 73.4 mmol, 2.0 eq) in MeOH (300 mL) was treated with formic acid (2 drops) followed by the dropwise addition of glyoxal (40% in H2O, 6.43 mL, 74.4 mmol, 1.0 eq) at rt. The solution was stirred at this temperature for 2 h and the methanol was evaporated under vaccum and replaced by pentane (300 mL). The solution was dried over anhydrous sodium sulfate, filtered and partially concentrated in vacuuo. Although good purity was obtained, the residual oil was preferably purified by flash column chromatography (silica gel, 10% Et2O in pentane to yield the pure desired diimine A as an orange solid (11.5 g, 72%). 1H NMR (400 MHz, CDCl3) δ 0.81 (24H, d, J=6.9 Hz, 8×CH3), 3.04 (4H, m, 4×CH), 3.87 (O—CH3), 6.79 (4H, s, 4×Hm-Ar), 8.14 (2H, s, 2×HC=N). 13C NMR (100 MHz, CDCl3) δ 23.3 (8×CH3), 28.1 (4×CH), 55.1 (2×O—CH3), 108.6 (4×CHm-Ar), 138.6 (4×CIVo-Ar), 141.6 (2×N—CIVAr), 157.2 (2×O—CIVAr), 163.5 (2×HC=N). HRMS (NSI+). found m/z [M H]+437.3158, calcd for C28H41O2N2 437.3163.

B—

N,N'-Bis-(4-methoxy-2,6-diisopropylphenylamino)ethane (B). A solution of diimine A (11.5 g, 26.3 mmol, 1.0 equiv) in anhydrous THF (200 mL) was cooled to −20° C. and treated with LiAlH4 (2.4 M in THF, 44.0 mL, 106 mmol, 4.0 equiv). Upon addition of LiAlH4, the yellow solution rapidly turned very dark purple and important bubbling was observed. After 15 min at −20° C., the colour of the reaction changed back to clear orange and the reaction was allowed to stir for 45 min at room temperature. The reaction was then cooled to 0° C., diluted with diethyl ether (200 mL), and carefully quenched with water (5.0 mL). After stirring for 10 min, a 15% aqueous solution of NaOH (5.0 mL) was added, followed by water (12 mL). The suspension was allowed to warm to room temperature and was stirred for 15 min before anhydrous magnesium sulfate was added until a fine solid was obtained. The solids were discarded by filtration and the filtrate was concentrated in vaccuo affording a clear orange and very viscous oil (11.80 g) in excellent purity. However, the oil was preferably purified by flash column chromatography (silica, 10-20% diethyl ether in pentane) to provide the pure desired diamine 25 as an orange viscous oil (11.35 g, 98%). 1H NMR (400 MHz, CDCl3) δ 1.26 (24H, d, J=6.9 Hz, 4×CH3), 3.08 (6H, vbs, 2×CH2+2×NH), 3.40 (4H, m, 4×CH), 3.82 (6H, m, 2×OCH3), 6.68 (4H, s, 4×Hm-Ar). 13C NMR (100 MHz, CDCl3) δ 24.2 (8×CH3), 27.9 (4×CH), 52.6 (2×CH2), 55.2 (2×OCH3), 108.9 (4×CHm-Ar), 136.4 (2×O—CIVp-Ar), 144.6 (4×CIVo-Ar), 156.2 (2×N—CIVAr). HRMS (NSI+). found m/z [M+H]+441.3470, calcd for C28H45O2N2 441.3476.

C—

1,3-Bis-(4-methoxy-2,4-diisopropylphenyl)imidazolinium chloride (SIPrOMe.HCl). A solution of diamine B (7.35 g, 16.7 mmol, 1.0 equiv) in triethyl orthoformate (60 mL) was heated to 120° C. and treated with the rapid addition of HCl (4.0 M in dioxane, 5.0 mL, 1.2 equiv). Upon addition of the HCl, the clear solution immediately turned into a white suspension and the stirring was continued for 10 min at 120° C. The reaction was cooled to room temperature and was diluted with pentane (60 mL). The white solid was isolated by filtration and washed with pentane (3×60 mL). After drying under high vacuum, the desired imidazolinium chloride C was obtained as a bright white powder (7.80 g, 96%). 1H NMR (400 MHz, CDCl3) δ 1.14 (12H, d, J=6.9 Hz, 4×CH3), 1.25 (12H, d, J=6.9 Hz, 4×CH3), 2.84 (4H, m, 4×CH), 3.74 (6H, m, 2×OCH3), 4.58 (4H, s, 2×N—CH2), 6.62 (4H, s, 4×Hm-Ar), 8.64 (1H, s, N=CH—N). 13C NMR (100 MHz, CDCl3) δ 23.3 (4×CH3), 25.1 (4×CH3), 29.1 (4×CH), 55.2 (2×OCH3), 109.8 (4×CHm-Ar), 121.9 (2×CHp-Ar), 147.4 (4×CIVo-Ar), 159.4 (N—CH—N), 161.1 (2×N—CIVAr). Anal. Calcd for C29H43ClN2O2: C, 71.51; H, 8.90; N, 5.75. Found: C, 71.40; H, 9.01; N, 5.85.

Procedure for the Preparation of Palladium Complexes

Synthesis of [Pd(IPent)(acac)Cl]

In a Schlenk flask equipped with a magnetic stirring bar were added IPent.HCl (IIIa) (215 mg, 0.4 mmole) and Pd(acac)2 (91 mg, 0.4 mmole) in dry 1,4-dioxane (6 mL) under an atmosphere of nitrogen. The reaction mixture was heated under reflux for 24 h. After this time, the dioxane was evaporated and the crude product dissolved in pentane.

The solution was filtered on a pad of silica covered with Celite and the product eluted with pentane. After evaporation of the solvent and drying under high vacuum, the desired complex was obtained as a yellow powder (183 mg, 82%).

1H NMR (300 MHz, CDCl3): δ=7.39 (t, J=8 Hz, 2H), 7.20 (d, J=8 Hz, 4H), 7.04 (s, 2H), 5.00 (s, 1H), 2.71 (m, 4H), 2.15 (m, 4H), 1.73 (s, 3H), 1.53 (s, 3H), 1.80-1.38 (m, 12H), 0.96 (t, J=7.3 Hz, 12H), 0.74 (t, J=7.4, 12H). Anal. Calcd for C40H59ClN2O2Pd: C, 64.77; H, 8.02; N, 3.78. Found: C, 64.86; H, 8.15; N, 3.82.

Procedure for the Synthesis of [Pd(IHept)(acac)Cl]

In a Schlenk flask equipped with a magnetic stirring bar were added IHept.HCl (IIIb) (260 mg, 0.4 mmole) and Pd(acac)2 (91 mg, 0.30 mmole) in dry 1,4-dioxane (6 mL) under an atmosphere of nitrogen. The reaction mixture was heated under reflux during 24 h. After this time, the dioxane was evaporated and the crude product dissolved in Et$_2$O.

The solution was filtered on a pad of silica covered with Celite and the product eluted with Et2O. After evaporation of the solvent and drying under high vacuum, the desired complex was obtained as a yellow powder (219 mg, 87%).

1H NMR (300 MHz, CDCl$_3$): δ=7.36 (t, J=7.8 Hz, 2H), 7.21 (d, 7.8 Hz, 4H), 7.02 (s, 2H), 4.98 (s, 1H), 2.82 (m, 4H), 2.17 (m, 4H), 1.77 (s, 3H), 1.40 (s, 3H), 1.73-1.25 (m, 20H), 1.15-1.08 (m, 8H), 0.80 (t, J=7.1 Hz, 24H). 13C NMR (CDCl$_3$, 75 MHz): 186.36, 184.05, 154.47, 144.77, 136.98, 129.32, 125.25, 99.94, 67.51, 39.99, 39.94, 39.74, 39.06, 26.86, 25.99, 21.95, 21.73, 21.22, 15.14. Anal. Calcd for C48H75ClN2O2Pd: C, 67.51; H, 8.85; N, 3.28. Found: C, 67.39; H, 8.77; N, 3.39.

Procedure for the Synthesis of [Pd(INon)(acac)Cl]

A similar procedure was employed to those discussed above for the IHept and IPent complexes.

Anal. Calcd for C56H91ClN2O2Pd: C, 69.61; H, 9.49; N, 2.90. Found: C, 69.67; H, 9.62; N, 3.01.

Procedure for the Synthesis of [Pd(IPent-OMe)(acac)Cl]

In a Schlenk flask equipped with a magnetic stirring bar were added IPentOMe.HCl (223 mg, 0.37 mmole) and Pd(acac)2 (85 mg, 0.28 mmole) in dry 1,4-dioxane (6 mL) under an atmosphere of nitrogen.

The reaction mixture was heated under reflux for 24 h. After this time, the dioxane was evaporated and the crude product dissolved in pentane. The solution was filtered on a pad of silica covered with Celite and the product eluted with pentane. After evaporation of the solvent and drying under high vacuum, the desired complex was obtained as a yellow powder (152 mg, 68%). Higher yield can be obtained on heating the reaction mixture for longer e.g. 82% after using a heating time of 40 h.

1H NMR (300 MHz, CDCl3): δ=7.01 (s, 2H), 6.73 (s, 4H), 5.04 (s, 1H), 3.86 (s, 2.66 (m, 4H), 2.11 (m, 4H), 1.78 (s, 3H), 1.61 (s, 3H), 1.75-1.40 (m, 12H), 0.97 (t, J=7.3 Hz, 12H), 0.75 (t, J=7.4 Hz, 12H). 13C NMR (CDCl3, 75 MHz): 186.57, 184.07, 159.89, 155.21, 145.94, 130.63, 125.68, 110.79, 100.17, 55.67, 41.93, 28.93, 27.85, 27.13, 26.42, 12.81, 11.93. Anal. Calcd for C42H63ClN2O4Pd: C, 62.91; H, 7.92; N, 3.49. Found: C, 62.84; H, 8.03; N, 3.53.

Procedure for the Synthesis of [Pd(IHept-OMe)(acac)Cl]

In a Schlenk flask equipped with a magnetic stirring bar were added IHeptOMe.HCl (193 mg, 0.27 mmole) and Pd(acac)2 (62 mg, 0.2 mmole) in dry 1,4-dioxane (5 mL) under an atmosphere of nitrogen.

The reaction mixture was heated under reflux for 24 h. After this time, the dioxane was evaporated and the crude product dissolved in pentane. The solution was filtered on a pad of silica covered with Celite and the product eluted with pentane. After evaporation of the solvent and drying under high vacuum, the desired complex was obtained as a yellow powder (150 mg, 82%). A higher yield (87%) was obtained after using a heating time of 40 h.

1H NMR (300 MHz, CDCl3): δ=6.96 (s, 2H), 6.70 (s, 4H), 4.99 (s, 1H), 3.84 (s, 3H), 2.76 (m, 4H), 2.10 (m, 4H), 1.76 (s, 3H), 1.46 (s, 3H), 1.68-1.04 (m, 20H), 0.79 (t, J=7.1 Hz, 24H). 13C NMR (CDCl3, 75 MHz): 186.36, 184.02, 178.93, 159.89, 154.88, 146.33, 130.42, 125.44, 110.49, 99.97, 55.68, 40.05, 28.92, 26.89, 26.13, 21.67, 21.17, 15.15. Anal. Calcd for C50H79ClN2O4Pd: C, 65.70; H, 8.71; Cl, N, 3.06. Found: C, 65.64; H, 8.80; N, 3.15.

Procedure for the Synthesis of [Pd(INon-OMe)(acac)Cl]

In a Schlenk flask equipped with a magnetic stirring bar were added INonOMe.HCl (221 mg, 0.27 mmole) and Pd(acac)2 (62 mg, 0.2 mmole) in dry 1,4-dioxane (5 mL) under an atmosphere of nitrogen. The reaction mixture was heated under reflux for 24 h. After this time, the dioxane was evaporated and the crude product dissolved in pentane.

The solution was filtered on a pad of silica covered with Celite and the product was eluted with pentane. After evaporation of the solvent and drying under high vacuum, the desired complex was obtained as a yellow powder (160 mg, 78%).

13C NMR (CDCl3, 75 MHz): 186.36, 183.83, 159.88, 154.87, 146.39, 130.45, 125.36, 110.47, 100.11, 59.69, 40.10, 37.45, 36.42, 30.88, 30.22, 27.02, 26.24, 23.94, 23.70, 14.59, 14.48. Anal. Calcd for C58H95ClN2O4Pd: C, 67.88; H, 9.33; N, 2.73. Found: C, 67.72; H, 9.46; N, 2.88.

Exemplary Reactions of [Pd(IPent-OMe)(acac)Cl], [Pd(IHept-OMe)(acac)Cl] and [Pd(INon-OMe)(acac)Cl]

Example 1 Amination with 4-fluoroanisole

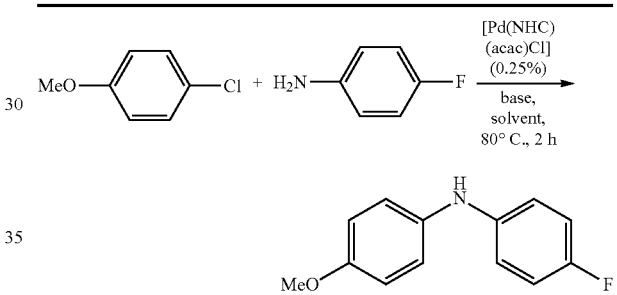

| Entry | Catalyst. | Solvent | Base | Conv.[b] |
|---|---|---|---|---|
| 1 | [Pd(IPent-OMe)(acac)Cl] | Toluene | KO$^t$Bu | 91 |
| 2 | [Pd(IPent-OMe)(acac)Cl] | Toluene | KO$^t$Am | 100 |
| 3 | [Pd(IPent-OMe)(acac)Cl] | Toluene | LiHMDS | 85 |
| 4 | [Pd(IPent-OMe)(acac)Cl] | 1,4-dioxane | KO$^t$Bu | 48 |
| 5 | [Pd(IPent-OMe)(acac)Cl] | 1,4-dioxane | KO$^t$Am | 35 |
| 6 | [Pd(IPent-OMe)(acac)Cl] | 1,4-dioxane | LiHMDS | 18 |
| 7 | [Pd(IPent-OPAe)(acac)Cl] | DME | KO$^t$Bu | 40 |
| 8 | [Pd(IPent-OMe)(acac)Cl] | DME | KO$^t$Am | 37 |
| 9 | [Pd(IPent-OMe)(acac)Cl] | DME | LiHMDS | 21 |
| 10 | [Pd(IPent-OMe)(acac)Cl] | DMF | KO$^t$Am | 23 |
| 11 | [Pd(IHept-OMe)(acac)Cl] | Toluene | KO$^t$Am | 100 |
| 12 | [Pd(INon-OMe)(acac)Cl] | Toluene | KO$^t$Am | 100 |

Reagents and conditions: 4-chloroanisole (0.5 mmol), 4-fluoroaniline (0.55 mmol), base (0.55 mmol), solvent (1.0 mL), catalyst (0.25 mol %). [b]Conversion to coupling product based on starting aryl chloride by GC, average of three runs. DME; dimethoxyethane.

As can be seen from the above table more polar solvents such as DME tended to give poorer results whilst the combination of toluene as solvent and KO$^t$Am as base can give 100% conversion.

Example 2

Amination with 4-fluoroaniline (entry 1, table below) and 3-trifluoromethylaniline (entry 2) at reduced catalyst loading.

4-Chloroanisole was reacted with the aniline using palladium catalysts with ITent or ITent-OMe as NHC ligands.

The results show that in each case the catalyst with the ITent-OMe ligand produced higher yields than the corresponding catalyst without the —OMe ligand. As the gain in activity is general with all of the ITent-OMe series, these results indicate the positive effect of the methoxy group. As the methoxy substituent resides away from the coordination sphere of the metal, the stronger σ-donor properties of ITent-OMe ligand compared with ITent ligands could explain the difference in the catalytic activity observed. This extra σ-donation may offer a greater stabilization of the Pd⁰—NHC complex. [Pd(IHept-OMe)(acac)Cl] combines the presence of the methoxy group and the optimal length of alkyl chain for C—N bond formation in these experiments.

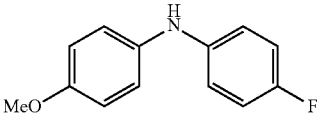 [SMILES: COc1ccc(Nc2ccc(F)cc2)cc1]

| Entry | Product | NHC ligand | GC conversions (%)$^d$ |
|---|---|---|---|
| 1$^b$ | (MeO-C₆H₄)-NH-(C₆H₄-F) | IPent | 58 |
| | | IPent-OMe | 70 |
| | | IHept | 82 |
| | | IHept-OMe | 98 |
| | | INon | 76 |
| | | INon-OMe | 86 |

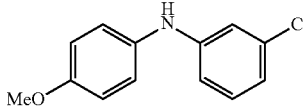

| Entry | Product | NHC ligand | GC conversions (%)$^d$ |
|---|---|---|---|
| 2$^c$ | (MeO-C₆H₄)-NH-(C₆H₄-CF₃) | IPent | 41 |
| | | IPent-OMe | 53 |
| | | IHept | 68 |
| | | IHept-OMe | 85 |
| | | INon | 64 |
| | | INon-OMe | 76 |

$^a$Reagents and conditions: ArCl (0.5 mmol), Ar'NH₂ (0.55 mmol), KO$^t$Am (0.55 mmol), toluene (1.0 mL). b 0.05 mol % Pd catalyst, 80° C., 3 h; c 0.1 mol % Pd catalyst, 110° C., 6 h. $^d$Conversion to coupling product based on starting aryl chloride by GC, average of three runs.

Example 3 Scope of the Buchwald-Hartwig Arylamination with [Pd(IHept-OMe)(acac)Cl]

| Entry | ArCl | Product | Catalyst (%) | Yield |
|---|---|---|---|---|
| 1 | 4-MeO-C₆H₄-Cl | (MeO-C₆H₄)-NH-(C₆H₄-F) | 0.05 | 95 |
| 2 | 2,6-dimethyl-C₆H₃-Cl | (2,6-Me₂-C₆H₃)-NH-(C₆H₄-F) | 0.05 | 91 |
| 3 | 2-MeO-C₆H₄-Cl | (2-MeO-C₆H₄)-NH-(C₆H₄-F) | 0.05 | 96 |
| 4 | 2,6-dimethyl-C₆H₃-Cl | (2,6-Me₂-C₆H₃)-NH-(2-F-C₆H₄) | 0.1 | 92 |

-continued $$\text{ArCl} + \text{Ar'NH}_2 \xrightarrow[\substack{\text{KO}^t\text{Am, toluene,} \\ 80\text{-}110°\text{ C.}}]{\substack{[\text{Pd(IHept-OMe)(acac)Cl}] \\ (0.05\text{-}0.2 \text{ mol \%})}} \text{Ar}\overset{\overset{\text{H}}{|}}{\underset{}{\text{N}}}\text{Ar}'$$

| Entry | ArCl | Product | Catalyst (%) | Yield |
|---|---|---|---|---|
| 5 | | | 0.1 | 87 |
| 6 | | | 0.1 | 79 |
| 7 | | | 0.1 | 74 |
| 8 | | | 0.2 | 91 |
| 9 | | | 0.2 | 88 |
| 10 | | | 0.2 | 90 |

-continued

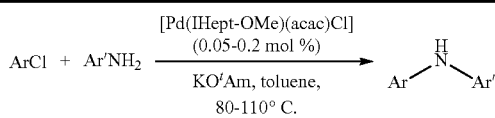

| Entry | ArCl | Product | Catalyst (%) | Yield |
|---|---|---|---|---|
| 11 | (2-chloro-1,3,5-trimethoxybenzene structure) | (N-(2,6-dimethylphenyl)-2,4,6-trimethoxyaniline structure) | 0.2 | 83 |

[a]Reagents and conditions: ArCl (0.5 mmol), Ar'NH$_2$ (0.55 mmol), KO$^t$Am (0.55 mmol), [Pd(IHept-OMe)(acac)Cl] (x mol %), toluene (1.0 mL), 80° C., 3 h.
[b]Isolated yields after chromatography on silica gel, average of two runs.
[c]110° C., 6 h.

The system, shown in the table above, displays excellent catalytic activity for the coupling of various substrates. Good yields are obtained with electron-poor anilines and electron-rich aryl chlorides, which are challenging coupling partners (entries 1-4 and 8-10). The system appears unaffected by the presence of substituents in the ortho-position of the aryl chlorides: couplings of 2-chloroanisole and 4-chloroanisole with 4-fluoroaniline gave very similar results (Entries 1 and 3). Similar results are observed for the coupling of 2-chloroanisole or 4-chloroanisole with 3-trifluoromethylaniline (Entries 8 and 9). Moreover, very good yields were obtained with sterically hindered substrates (Entries 4, 6 and 11). The increased conformational flexibility of IHept-OMe may allow it to better accommodate sterically hindered substrates in the coordination sphere of the metal center. Finally, various anilines were successfully coupled with deactivated 1,3-dimethoxychlorobenzene (entries 5, 6 and 9) and, for the first time, with very deactivated 1,3,5-trimethoxychlorobenzene at low catalyst loading (entry 10), attesting to the high reactivity of [Pd(IHept-OMe)(acac)Cl].

Example 4

The Efficiency of Catalyst, [Pd(IHept-OMe)(acac)Cl] with more nucleophilic amines was also tested.

Non-activated aryl chlorides were successfully coupled with N-methylaniline at low catalyst loadings (as low as 50 ppm of [Pd(IHept-OMe)(acac)Cl]); remarkable catalyst productivity-turnover number [TON] up to 18,000 or more, was observed (Entries 2 and 3 in the table below). These results are comparable with results obtained with the most efficient Pd/phosphine systems for similar substrates.

ArCl + H-N(Me)-Ph → [Pd(IHept-OMe)(acac)Cl] (50-200 ppm), KO$^t$Am, toluene, 110° C. → Ar-N(Me)-Ph

| Entry | Product | [Pd(IHept-OMe)(acac)Cl] (ppm) | Yield (%)[b] | TON |
|---|---|---|---|---|
| 1 | (2-methyl-N-methyl-N-phenylaniline) | 0 (control) | 0 | |
| 2 | (2-methyl-N-methyl-N-phenylaniline) | 50 | 91 | 18200 |
| 3 | (3-methyl-N-methyl-N-phenylaniline) | 50 | 93 | 18600 |
| 4 | (4-methyl-N-methyl-N-phenylaniline) | 100 | 84 | 8400 |
| 5 | (4-methoxy-N-methyl-N-phenylaniline) | 200 | 83 | 4150 |

[a]Reagents and conditions: ArCl (0.5 mmol), Ar'NH$_2$ (0.55 mmol), KO$^t$Am (0.55 mmol), [Pd(IHept-OMe)(acac)Cl] (x ppm), toluene (1.0 mL), 110° C.
[b]Isolated yields after chromatography on silica gel, average of two runs.

Preparation of [Pd(NHC)(cinnamyl)Cl]:
General Procedure

In a glovebox (under a nitrogen atmosphere), in a round bottom flask equipped with a magnetic stirring bar were added the NHC·HCl imidazolium salt precursor (2.2 eq) and KO$^t$Bu (2.4 eq) in THF. In these examples IPent.HCl, IHept.HCl and INon.HCl were employed.

The reaction mixture was stirred at room temperature for 3 h and then [Pd(cinnamyl)(μ-Cl)]$_2$ (1 eq) was added. The reaction mixture was then stirred overnight at room temperature.

After this time, outside the glovebox, the THF was evaporated and the crude product was dissolved in DCM, filtered on a pad of celite and eluted with DCM. After evaporation of the solvent, the complex was dissolved in pentane and passed through a frit (sintered glass filter). The pentane was evaporated and after drying under high vacuum, the pure complex was obtained.

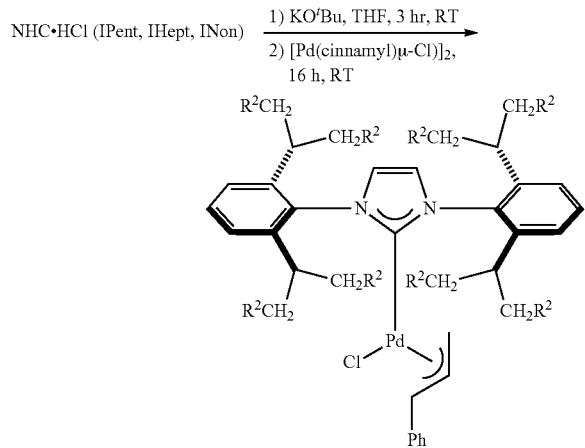

[Pd(IPent)(cinnamyl)Cl]:

The general procedure starting from 0.425 mmol of [Pd(cinnamyl)(μ-Cl)]$_2$ yielded the complex as a yellow powder (600 mg, 93%).

The pentane was evaporated rapidly using a Schlenk line, yielding the complex as a foam which was crumbled to a powder.

$^1$H NMR (400 MHz, C$_6$D$_6$): δ 7.31-7.26 (m, 2H, H$_{Ar}$), 7.19 (t, J=7.7 Hz, 2H, H$_{Ar}$), 7.04 (d, J=7.7 Hz, 4H, H$_{Ar}$), 7.04-6.93 (m, 3H, H$_{Ar}$), 6.63 (s, 2H, H$_{Im}$), 5.23 (dt, J=12.8 Hz; J'=9.3 Hz, 1H, H$_{cin}$), 4.54 (d, J=12.8 Hz, 1H, H$_{cin}$), 2.89-2.50 (m, br, 5H, CH+H$_{cin}$), 2.23-2.06 (m, br, 4H, CH$_2$), 1.82-1.36 (m, br, 13H, CH$_2$+H$_{cin}$), 1.23-1.03 (m, br, 12H, CH$_3$), 0.76 (t, J=7.4 Hz, 12H, CH$_3$). $^{13}$C NMR (100 MHz, CD$_2$Cl$_2$): δ 182.1 (NCN), 144.5 (br, C$_{Ar}$), 138.4 (C$_{Ar}$), 138.2 (C$_{Ar}$), 129.1 (CH$_{Ar}$), 128.5 (CH$_{Ar}$), 127.6 (CH$_{Ar}$), 126.9 (CH$_{Ar}$), 125.3 (br, CH$_{Ar}$), 124.9 (CH$_{Im}$), 108.5 (C$_{cin}$), 90.5 (C$_{cin}$), 46.5 (C$_{cin}$), 42.1 (CH), 28.3 (CH$_2$), 27.9 (CH$_2$), 13.1 (CH$_3$), 11.5 (br, CH$_3$). Anal. Calcd. for C$_{44}$H$_{61}$ClN$_2$Pd: C, 69.55; H, 8.09; N, 3.69. Found: C, 69.52; H, 8.03; N, 3.75.

[Pd(IHept)(cinnamyl)Cl]:

The general procedure starting from 0.35 mmol of [Pd(cinnamyl)(μ-Cl)]$_2$ yielded the complex as an orange powder (605 mg, 99%).

The pentane was evaporated rapidly using a Schlenk line, yielding the complex as a foam which was crumbled to a powder.

$^1$H NMR (400 MHz, C$_6$D$_6$): δ 7.38-7.34 (m, 2H, H$_{Ar}$), 7.23 (t, J=7.9 Hz, 2H, H$_{Ar}$), 7.10 (d, J=7.9 Hz, 4H, H$_{Ar}$), 7.05-7.00 (m, 2H, H$_{Ar}$), 6.98-6.94 (m, 1H, H$_{Ar}$), 6.83 (s, 2H, H$_{Im}$), 5.26 (dt, J=12.9 Hz; J'=9.2 Hz, 1H, H$_{cin}$), 4.64 (d, J=12.9 Hz, 1H, H$_{Cin}$), 2.93-2.66 (m, br, 5H, CH+H$_{Cin}$), 2.18-2.05 (m, 4H, CH$_2$), 1.78-1.34 (m, 21H, CH$_2$+H$_{Cin}$), 1.25-1.11 (m, 8H, CH$_2$), 1.11-0.94 (m, 12H, CH$_3$), 0.82 (t, J=7.2 Hz, 12H, CH$_3$). $^{13}$C NMR (100 MHz, CD$_2$Cl$_2$): δ 181.8 (NON), 145.1 (br, C$_{Ar}$), 138.5 (C$_{Ar}$), 137.8 (C$_{Ar}$), 129.2 (CH$_{Ar}$), 128.5 (CH$_{Ar}$), 127.7 (CH$_{Ar}$), 126.9 (CH$_{Ar}$), 125.2 (br, CH$_{Ar}$), 124.9 (CH$_{Im}$), 108.5 (C$_{cin}$), 91.1 (C$_{cin}$), 46.0 (C$_{cin}$), 39.7 (CH), 39.5 (CH$_2$), 38.4 (CH$_2$), 22.0 (CH$_2$), 20.9 (CH$_2$), 14.9 (CH$_3$), 14.8 (CH$_3$). Anal. Calcd. for C$_{52}$H$_{77}$ClN$_2$Pd: C, 71.62; H, 8.90; N, 3.21. Found: C, 71.75; H, 8.84; N, 3.18.

[Pd(INon)(cinnamyl)Cl]:

The general procedure starting from 0.113 mmol of [Pd(cinnamyl)(μ-Cl)]$_2$ yielded the complex as a yellow/green powder (200 mg, 90%).

After evaporation of the pentane, the complex remained an oil. It solidified slowly after a few weeks storage inside a glovebox (under an N$_2$ atmosphere).

$^1$H NMR (400 MHz, C$_6$D$_6$): δ 7.40-7.36 (m, 2H, H$_{Ar}$), 7.25 (t, J=7.7 Hz, 2H, H$_{Ar}$), 7.13 (d, J=7.7 Hz, 4H, H$_{Ar}$), 7.06-7.01 (m, 2H, H$_{Ar}$), 7.00 (s, 2H, H$_{Im}$), 6.98-6.94 (m, 1H, H$_{Ar}$), 5.28 (dt, J=12.9 Hz; J'=9.3 Hz, 1H, H$_{cin}$), 4.68 (d, J=12.9 Hz, 1H, 2.99-2.71 (m, br, 5H, CH+H$_{Cin}$), 2.24-2.10 (m, br, 4H, CH$_2$), 1.89-1.34 (m, 29H, CH$_2$+H$_{Cin}$), 1.28-1.15 (m, 16H, CH$_2$), 1.09-0.97 (m, 12H, CH$_3$), 0.89-0.82 (m, 12H, CH$_3$). $^{13}$C NMR (100 MHz, CD$_2$Cl$_2$): δ 181.9 (NCN), 145.2 (br, C$_{Ar}$), 138.6 (C$_{Ar}$), 137.7 (C$_{Ar}$), 129.2 (CH$_{Ar}$), 128.5 (CH$_{Ar}$), 127.7 (CH$_{Ar}$), 126.9 (CH$_{Ar}$), 125.2 (br, CH$_{Ar}$), 124.9 (CH$_{Im}$), 108.7 (C$_{cin}$), 91.0 (C$_{cin}$), 46.0 (C$_{cin}$), 39.8 (CH), 36.9 (CH$_2$), 35.9 (CH$_2$), 31.3 (br, CH$_2$), 29.9 (br, CH$_2$), 23.9 (CH$_2$), 23.7 (CH$_2$), 14.5 (CH$_3$), 14.2 (CH$_3$). Anal. Calcd. for C$_{60}$H$_{93}$ClN$_2$Pd: C, 73.22; H, 9.52; N, 2.85. Found: C, 73.40; H, 9.69; N, 2.84.

REFERENCES

1. Huang, J.; Nolan, S. P. J. Am. Chem. Soc. 1999, 121, 9889-9890.
2. Steele, B. R.; Georgakopoulos, S.; Micha-Screttas, M.; Screttas, C. G., Eur. J. Org. Chem., 2007, 19, 3091-3094.
3. a) Organ, M. G.; Ç alimsiz, S.; Sayah, M.; Hoi, K. H.; Lough, A. J. Angew. Chem., 2009, 121, 2419-2423; b) Organ, M. G.; Ç alimsiz, S.; Sayah, M. Mallik, D., Angew. Chem. Int. Ed., 2010, 49, 2014-2017; c) Organ, M. G.; Dowlut, M., Mallik, D. Eur. J. Chem., 2010, 16, 4279-4283; d) Organ, M. G.; Ç alimsiz, S., Chem. Commum., 2011, 47, 5181-5183; e) Sayah, M.; Organ, M. G., Eur. J. Chem., 2011, 17, 11719-11722; f) Hoi, K. H.; Ç alimsiz, S.; Froese, R. D. J.; Hopkinson, A. C.; Organ, M. G., Eur. J. Chem., 2011, 17, 3086-3090; g) Valente, C.; Ç alimsiz, S.; Hoi, K. H.; Mallik, D.; Sayah, M.; Organ, M. G., Angew. Chem. Int. Ed., 2012, 51, 3314-3332; h) Hoi, K. H.; Ç alimsiz, S.; Froese, R. D. J.; Hopkinson, A. C.; Organ, M. G., Eur. J. Chem., 2012, 18, 145-151; i) Valente, C.; Belowich, M. E.; Hadei, N.; Organ, M. G., Eur. J. Org. Chem., 2010, 23, 4343-4354; j) Hoi, K. H.; Organ, M. G., Eur. J. Chem., 2012, 18, 804-807; k) McCann, L. C.; Hunter, H. N.; Clyburne, J. A. C.; Organ, M. G., Angew. Chem. Int. Ed., 2012, 51(28), 7024-7027.

The invention claimed is:

1. A method of preparing an at least 2,6 disubstituted aniline, the method comprising: reacting a 2-amino isophthalic acid diester with sufficient Grignard reagent R$^2$CH$_2$MgX to form the corresponding diol product,
wherein X is chloride, bromide or iodide, and R$^2$ is selected from H, methyl, ethyl, n-propyl and

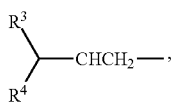

wherein either $R^3$ is H and $R^4$ is alkyl that may be substituted, or
each of $R^3$, $R^4$ are an independently selected alkyl that may be substituted;
dehydrating the diol product to the corresponding dialkene; and
hydrogenating the dialkene product to form the corresponding aniline.

2. The method of claim 1, wherein the 2-amino isophthalic acid diester has H in the meta and para positions to provide an aniline of general formula I, wherein the groups $Z_1$, $Z_2$, and $Z_3$ are H:

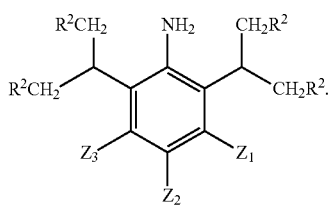

I

3. The method of claim 2, further comprising substitution of one or more of the H groups $Z_1$, $Z_2$, and $Z_3$ with a substituent independently selected from the group consisting of: —I, —$CF_3$, —$OR^6$, —$R^6$ and —$NR^7_2$;
wherein each group $R^5$, $R^6$ or $R^7$ is independently selected from the group consisting of alkyl that may be unsaturated, substituted alkyl that may be unsaturated, aryl, substituted aryl, aralkyl and substituted aralkyl.

4. The method of claim 3, wherein $Z_1$, and $Z_3$ are H and $Z_2$ is selected from the group consisting of —I, —$CF_3$, —$OR^5$, —$R^6$ and —$NR^7_2$.

5. The method according to claim 1, wherein the 2-amino isophthalic acid diester is of formula X:

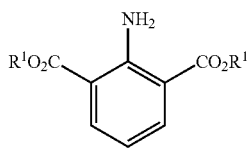

X wherein each group $R^1$ is independently selected from the group alkyl, benzyl and substituted benzyl.

6. The method of claim 1, wherein the 2-amino isophthalic acid diester has a substituent Z provided in one or more of the positions meta or para to the amino group;
wherein each Z is independently selected from the group consisting of —I, —$CF_3$, —$OR^5$, —$R^6$ and —$NR^7_2$, wherein each group $R^5$, $R^6$ or $R^7$ is independently selected from the group consisting of: alkyl that may be unsaturated, substituted alkyl that may be unsaturated, aryl, substituted aryl, aralkyl and substituted aralkyl.

7. The method of claim 1, wherein the 2-amino isophthalic acid diester is of general formula Xa:

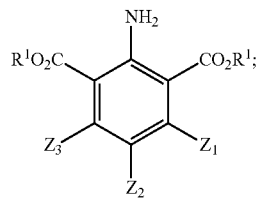

Xa wherein each group $Z_1$, $Z_2$ and $Z_3$ is independently selected from the group consisting of —H, —I, —$CF_3$, —$OR^5$, —$R^6$ and —$NR^7_2$, wherein each group $R^5$, $R^6$ or $R^7$ is independently selected from the group consisting of alkyl that may be unsaturated, substituted alkyl that may be unsaturated, aryl, substituted aryl, aralkyl and substituted aralkyl.

8. The method of claim 1, wherein the dehydration of the diol product is by use of sulfuric acid.

9. The method of claim 1, wherein the hydrogenation of the dialkene is by $H_2$ in the presence of a catalyst.

10. The method of claim 1, further comprising preparation of the 2-amino isophthalic acid diester by:
the bis-oxidation of 2-nitro-m-xylene to 2-nitroisophthalic acid;
the conversion of 2-nitroisophthalic acid to a corresponding nitro diester; and
the reduction of the nitro diester to the 2-amino isophthalic acid diester.

11. The method of claim 10, wherein the bis-oxidation of 2-nitro-m-xylene to 2-nitroisophthalic acid is by means of alkaline potassium permanganate.

12. The method of claim 10, wherein the reduction of the nitro diester to the 2-amino isophthalic acid diester is by $H_2$ in the presence of a catalyst.

13. The method of claim 1, wherein $R^2$ is selected from H, methyl, ethyl and n-propyl.

14. An aniline of formula VII or formula VIII:

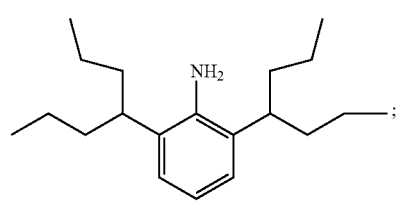

VII

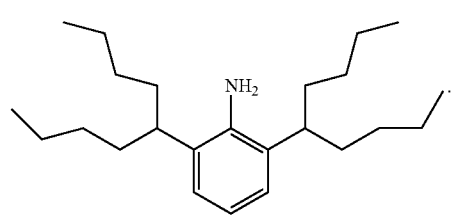

VIII

* * * * *

UNITED STATES PATENT AND TRADEMARK OFFICE
CERTIFICATE OF CORRECTION

| | |
|---|---|
| PATENT NO. | : 9,890,125 B2 |
| APPLICATION NO. | : 14/759595 |
| DATED | : February 13, 2018 |
| INVENTOR(S) | : Steven P. Nolan and Sebastien Meiries |

It is certified that error appears in the above-identified patent and that said Letters Patent is hereby corrected as shown below:

In Column 43, Claim 3, Line 34 please change the fourth line of text to correctly list the superscript. The full line of text is below:

of: -I, -CF$_3$, -OR$^5$, -R$^6$ and -NR$^7$$_2$;

Signed and Sealed this
Tenth Day of July, 2018

Andrei Iancu
*Director of the United States Patent and Trademark Office*